US009050283B2

(12) United States Patent
Levine et al.

(10) Patent No.: US 9,050,283 B2
(45) Date of Patent: Jun. 9, 2015

(54) **BROAD SPECTRUM VACCINE AGAINST NON-TYPHOIDAL *SALMONELLA***

(75) Inventors: Myron M. Levine, Columbia, MD (US); Raphael Simon, Baltimore, MD (US); James Galen, Sykesville, MD (US); Sharon Tennant, Baltimore, MD (US)

(73) Assignee: University of Maryland, Baltimore, Baltimore, MD (US)

(*) Notice: Subject to any disclaimer, the term of this patent is extended or adjusted under 35 U.S.C. 154(b) by 538 days.

(21) Appl. No.: 13/144,336

(22) PCT Filed: Jan. 16, 2010

(86) PCT No.: PCT/US2010/021289
§ 371 (c)(1), (2), (4) Date: Jul. 13, 2011

(87) PCT Pub. No.: WO2010/083477
PCT Pub. Date: Jul. 22, 2010

(65) Prior Publication Data

US 2011/0274714 A1 Nov. 10, 2011

Related U.S. Application Data

(60) Provisional application No. 61/145,124, filed on Jan. 16, 2009.

(51) Int. Cl.

| | |
|---|---|
| ***A61K 39/112*** | (2006.01) |
| ***A61K 39/00*** | (2006.01) |
| ***A61K 39/385*** | (2006.01) |
| ***A61K 45/00*** | (2006.01) |
| ***A61K 47/00*** | (2006.01) |

(52) U.S. Cl.
CPC ....... *A61K 39/0275* (2013.01); *A61K 2039/522* (2013.01); *A61K 2039/6068* (2013.01); *A61K 2039/627* (2013.01)

(58) Field of Classification Search
CPC .................... A61K 39/0275; A61K 2039/522; A61K 2039/545; A61K 2039/55544; A61K 2039/6068; A61K 2039/521; A61K 2039/53; A61K 2039/55505; A61K 2039/55555; A61K 2039/627; A61K 39/00; A61K 39/025; A61K 39/0258; A61K 39/07; A61K 39/092; A61K 39/116; A61K 39/385; A61K 38/193; C12N 1/00; C12N 15/00; C12N 1/36; C12N 15/70; C07K 14/245; C07K 16/18; C07K 2319/00; C12Q 1/689; C12Q 2600/158
USPC ......... 424/197.11, 93.48, 194.1, 235.1, 258.1
See application file for complete search history.

(56) References Cited

U.S. PATENT DOCUMENTS 6,130,082 A 10/2000 Majarian
8,137,930 B2 * 3/2012 Vindurampulle et al. ... 435/69.1

FOREIGN PATENT DOCUMENTS

| | | | |
|---|---|---|---|
| WO | 2007/053489 | A2 | 5/2007 |
| WO | WO 2007/053489 | A2 | 5/2007 |
| WO | 2007/106956 | A1 | 9/2007 |
| WO | WO 2007/106956 | A1 | 9/2007 |
| WO | 2010/101750 | A2 | 9/2010 |

OTHER PUBLICATIONS

Zuniga et al., Journal of Clinical Microbiology, 2005; 43(9):4545-4550.*

Alekseeva et al., Immunologiya (Moscow, Russian Federation), 1986; 1: 32-36 (abstract only attached).*

Wang et al., Infection and Immunity, 2001; 69(8): 4734-4741.*

Matsui et al., Oral Immunization with ATP-Dependent Protease-Deficient Mutants Protects Mice against Subsequent Oral Challenge with Virulent *Salmonella enterica* Serovar Typhimurium, Infection and Immunity, 71: 30-39 (2003).

Watson et al., Protection of Mice against *Salmonella* typhimunium with an O-Specific Polysaccharide-Protein Conjugate Vaccine, Infection and Immunity, 60: 4679-4686 (1992).

McDermott et al., High-Affinity Interaction between Gram-Negative Flagellin and a Cell Surface Polypeptide Results in Human Monocyte Activation, Infection and Immunity, 68: 5525-5529 (2000).

Brett et al., Structural and Immunological Characterization of *Burkholderia pseudomallei* O-Polysaccharide-Flagellin Protein Conjugates, Infection and Immunity, 64: 2824-2828 (1996).

Svenson et al., Artificial *Salmonella* Vaccines: *Salmonella typhimurium* O-Antigen-Specific Oligosaccharide-Protein Conjugates Elicit Protective Antibodies in Rabbits and Mice, Infection and Immunity, 32: 490-496 (1981).

Das Gracas Luna et al., *Salmonella* flagellin fused with a linear epitope of colonization factor antigen I (CFA/I) can prime antibody responses against homologous and heterologous fimbriae of enterotoxigenic *Escherichia coli*, Research in Microbiology, 151: 575-582 (2000).

Simon et al., *Salmonella enterica* Serovar Enteritidis Core O Polysaccharide Conjugated to H:g,m Flagellin as a Candidate Vaccine for Protection against Invasive Infection with S. Enteritidis, Infection and Immunity, 79: 4240-4249 (Oct. 2011).

Brett et al., Structural and Immunological Characterization of *Burkholderia* . . . , Infection and Immunity, 64(7):2824-2828 (1996), Amer. Soc. for Microbiol., Washington, D.C.

(Continued)

*Primary Examiner* — Gary Nickol
*Assistant Examiner* — Lakia Tongue
(74) *Attorney, Agent, or Firm* — Nevrivy Patent Law Group P.L.L.C.

(57) ABSTRACT

The present invention is drawn to attenuated *Salmonella* serovar strains *S. Typhimurium* and *S. Enteritidis*, conjugate vaccines derived from these attenuated strains of *S. Typhimurium* and *S. Enteritidis*, comprising an O polysaccharide covalently linked to a flagellin protein, and methods for inducing an immune response in a subject comprising administering the attenuated strains and/or the conjugate vaccines of the invention.

20 Claims, 10 Drawing Sheets

(56) References Cited

OTHER PUBLICATIONS

Matsui et al., Oral Immunization with ATP-Dependent Protease-Deficient . . . , Infection and Immunity, 71(1):30-39 (2003), Amer. Soc. for Microbiol., Washington, D.C.

McDermott et al., High Affinity Interaction between Gram-Negative . . . , Infection and Immunity, 68(10):5525-5529 (2000), Amer. Soc. for Microbiol., Washington, D.C.

Watson et al., Protection of Mice Against *Salmonella typhimurium* . . . , Infection and Immunity, 60(11):4679-4686 (1992), Amer. Soc. for Microbiol., Washington, D.C.

* cited by examiner

BROAD SPECTRUM VACCINE AGAINST NON-TYPHOIDAL *SALMONELLA*

CROSS REFERENCE TO RELATED APPLICATIONS

This application is the U.S. National Stage Application under 35 U.S.C. §371 of International Application No. PCT/US2010/021,289, with an international filing date of Jan. 16, 2010, which claims the benefit of U.S. Appl. No. 61/145,124, filed Jan. 16, 2009. The content of the aforesaid application is relied upon and incorporated by reference in its entirety.

STATEMENT OF FEDERALLY SPONSORED RESEARCH AND DEVELOPMENT

This invention was made with government support under Grant No. AI057168 awarded by the National Institutes of Health. The government has certain rights in the invention.

REFERENCE TO A SEQUENCE LISTING SUBMITTED ELECTRONICALLY VIA EFS-WEB

The content of the sequence listing (Name: Sequence_Listing.txt, Size: 28,327 bytes; and Date of Creation: Jan. 16, 2010) electronically submitted via EFS-Web is incorporated by reference in its entirety.

FIELD OF THE INVENTION

The present invention generally relates at least to the fields of immunology, molecular biology, infectious disease and medicine. In particular, the invention relates to conjugate vaccines for non-typhoidal *Salmonella* infections, attenuated non-typhoidal *Salmonella* strains, and to the use of those strains in heterologous mucosal prime/parenteral boost immunization strategies which can be used to markedly broaden the immune responses elicited over what can be currently achieved with oral vaccine or conjugates alone.

BACKGROUND OF THE INVENTION

Bacteriology of the Complex Genus *Salmonella*

Only two species are currently recognized within the genus *Salmonella, Salmonella enterica* and *Salmonella bongori*, and only the former is important with respect to human disease. There are six subspecies of *Salmonella enterica*, of which subspecies I, *S. enterica* subspecies *enterica*, contains all the important pathogens that cause human disease. *S. enterica* subspecies *enterica* is further sub-divided into more than 2500 serovars (i.e., distinct serotypes) based on the presence of specific somatic O antigens, capsular polysaccharide surface Vi antigen and flagellar H antigens expressed by the organism. The antigenic serotyping scheme (previously called the Kauffman-White scheme and more recently the White-Kauffmann-Le Minor scheme) defines a serovar (i.e., serotype) by its O polysaccharide antigens (and also whether capsular polysaccharide Vi is expressed) and its H flagella antigens. The serogroup of a *Salmonella* is defined by its O antigens, while the serovar is defined by the full antigenic structure that includes all the flagellar antigens and whether Vi polysaccharide is expressed. O antigens are part of the lipopolysaccharide (LPS) surface structure that is part of the outer membrane of the bacteria. The lipid A (endotoxin) portion of the LPS, is a glucosamine-based phospholipid that makes up the outer monolayer of the outer membrane of the bacteria. Attached to the lipid A is a core polysaccharide that is essentially identical in all the important *Salmonella* serovars that cause human disease, particularly invasive disease. The more internal portion of the core polysaccharide is the "inner core", while the more external portion is the "outer core" (FIG. 1). Finally, the most external surface component that is attached to the outer core polysaccharide is a terminal O polysaccharide that consists of terminal O repeat units linked one to another; this is what is exposed to the environment. The terminal O polysaccharide varies in structure depending on the sugars comprising the core unit and their linkages one to another. Many of the most important *Salmonella* serovars associated with human disease fall into serogroup B and serogroup D. The O repeat units of *Salmonella* serogroups B and D share a common trisaccharide backbone that consists of repeats of mannose-rhamnose and galactose (Wyk P and Reeves P. *J. Bacteriol.* 1989; 171:5687-5693). This backbone is the structure for the common *Salmonella* epitope 12 that is found in serogroup B (4,[5],12) and Group D (9, 12). Attached to the backbone is another dideoxyhexose sugar that is alpha 1,3-linked to the mannose residue. If that dideoxyhexose sugar is abequose, the resultant structure constitutes the immunodominant antigen "4" that defines O serogroup B. If the dideoxyhexose sugar that is alpha 1,3-linked to mannose is tyvelose, the resultant structure creates immunodominant antigen "9" that defines O serogroup D.

Some *Salmonella* can express two different antigenic forms of flagella, called Phase 1 and Phase 2. *Salmonella Typhimurium* has the antigenic scheme 1,4,(5),12:i:1,2. This indicates that it falls within O serogroup B (defined by antigen 4), expresses minor O antigens 1 and 12 and sometimes antigen 5 and expresses Phase 1 flagella which manifest antigen H:i and Phase 2 flagella which manifest antigen H:1,2.

The serovars within *Salmonella enterica* subspecies *enterica* that can cause disease in humans can be divided into three broad clinico-pathological-epidemiologic categories that differ in clinical presentation, pathogenesis and epidemiology:

Enteric Fever

*Salmonella enterica* serovars *Typhi* (*S. Typhi*) and *Salmonella enterica* serovars *Paratyphi* A and B (*S. Paratyphi* A and *S. Paratyphi* B) cause, respectively, typhoid and paratyphoid fevers (collectively known as enteric fevers). Enteric fevers are febrile illnesses characterized by infection of the gut associated lymphoid tissue, liver, spleen, bone marrow and gall bladder and accompanied by a low level bacteremia (Levine M M. Typhoid Fever Vaccines. In: Plotkin S A, Orenstein W A, editors. Vaccines. Fourth ed. Philadelphia: Saunders; 2004. P. 1057-93). Sequencing of the *S. Typhi* and *S. Paratyphi* A genomes has revealed an impressive degree of homology (Parkhill J et al., Nature 2001; 413:848-52; Deng W et al., *J. Bacteriol.* 2003; 185:2330-7; McClelland M et al., *Nat. Genet.* 2004; 36:1268-74).

Septicemias and Metastatic Focal Infections

A second (uncommon) set of *Salmonella* serovars, including *S. Choleraesuis* and *S. Paratyphi* C are characterized by their propensity to cause septicemia (*Salmonella* in the blood, accompanied by physiological derangements), multiple organ dysfunction and metastatic purulent infections such as osteomyelitis and focal abscesses (Saphra I, and Wasserman M. *Am. J. Med. Sci.* 1954; 228:525-33; Chen P L et al., *J Microbiol. Immunol. Infect.* 2007; 40:240-7).

Gastroenteritis and invasive disease caused by non-typhoidal *Salmonella* (NTS)

The third set of *Salmonella*, commonly called non-typhoidal *Salmonella* (NTS) serovars, includes a large number of serovars that cause gastroenteritis (vomiting, fever and diarrhea). In healthy hosts NTS gastroenteritis is usually a self-limited clinical illness and is quite common. By contrast, in young infants, the elderly and immunocompromised hosts, NTS can cause severe and fatal disease in the U.S. (Vugia D J et al., *Clin. Infect. Dis.* 2004; 38 Suppl 3:S149-S156; Kennedy M et al., *Clin. Infect. Dis.* 2004; 38 Suppl 3:S142-S148; Voetsch A C et al., *Clin. Infect. Dis.* 2004; 38 Suppl 3:5127-34:5127-5134; Adak G K et al., *Gut* 2002; 51:832-41) and abroad (Adak G K et al., *Gut* 2002; 51:832-41; Graham S M et al., *Pediatr. Infect. Dis. J.* 2000; 19:1189-96; Walsh A L et al., *Pediatr. Infect. Dis. J.* 2000; 19:312-8; Berkley J A et al., *N. Engl. J. Med.* 2005; 352:39-47; Kariuki S et al., *BMC. Microbiol.* 2006; 6:101; Kariuki S et al., *J. Med. Microbiol.* 2006; 55:585-91; Hill P C et al., *BMC. Infect. Dis.* 2007; 7:2; Ikumapayi U N et al., *J. Med. Microbiol.* 2007; 56:1479-84; Levy H et al., *J. Clin. Microbiol.* 2008; 46:1861-6). In sub-Saharan Africa, invasive disease associated with NTS often occurs without accompanying gastroenteritis. While non-typhoidal *Salmonella* (NTS) has long been known to be a cause of gastroenteritis, as noted by some of the above-cited documents, it is becoming increasingly recognized both in the U.S. and globally, that multiple antibiotic-resistant strains are also emerging as important causes of invasive bacteremia and focal infections, resulting in hospitalizations and deaths.

Predominant NTS Serovars and Epidemiologic Insights

In the U.S. and Europe, a relatively small number of *Salmonella* account for the vast majority of cases of gastroenteritis and two serovars, *S. Typhimurium* and *S. Enteritidis*, account for 45-60% of all cases (Voetsch A C et al., *Clin. Infect. Dis.* 2004; 38 Suppl 3:S127-34:S127-S134; Adak G K et al., *Gut* 2002; 51:832-41). In certain age groups (e.g., infants), the incidence is high (estimated by the US Centers for Disease Control to be approximately 120 cases per 100, 000 infants) (Vugia D J et al., *Clin. Infect. Dis.* 2004; 38 Suppl 3:S149-56:S149-S156). In young infants (<3 months age), the elderly and immunocompromised hosts (e.g., on chemotherapy for cancer or autoimmune diseases), NTS often leads to severe clinical disease, meningitis and death (Vugia D J et al., *Clin. Infect. Dis.* 2004; 38 Suppl 3:S149-5156; Kennedy M et al., *Clin. Infect. Dis.* 2004; 38 Suppl 3:S142-S148). Among infants and elderly (>60 years), 25% and 47% of all reported cases, respectively, end up hospitalized (Kennedy M et al., *Clin. Infect. Dis.* 2004; 38 Suppl 3:5142-S148). Increasingly, NTS strains associated with invasive disease are being identified that are difficult to treat because of their resistance to multiple, clinically relevant, antibiotics (Varma J K et al., *J. Infect. Dis.* 2005; 191:554-61). Such multi-resistant strains make invasive NTS disease an important infectious disease problem (Id.). In the USA, the Foodborne Diseases Active Surveillance Network (FoodNet), a component of the Emerging Infections Program of the Centers for Disease Control, coordinates active surveillance for food-borne disease and undertakes studies to elucidate the epidemiology of foodborne diseases and to evaluate interventions to diminish disease burden. Notably, whereas the incidence of disease caused by other important enteric pathogens such as *Campylobacter jejuni* and enterohemorrhagic *Escherichia coli* has been halved consequent to interventions initiated by FoodNet, the incidence of NTS has remained the same. The failure of interventions that are effective against other bacterial enteropathogens to diminish the NTS disease burden makes vaccination against NTS an attractive option. In Africa, invasive NTS is a major killer of infants and toddlers (ages 3-11) and >80% of the cases are caused by *S. Typhimurium* and *S. Enteritidis*.

NTS and Biodefense

The largest bioterror incident ever in the USA involved *S. Typhimurium* (Torok T J et al., *JAMA* 1997; 278:389-95). Members of a religious commune deliberately contaminated salad bars in restaurants, leading to a protracted outbreak of gastrointestinal illness that resulted in 751 cases (Id.). Because NTS outbreaks in the USA are not uncommon (Braden C R. Clin. Infect. Dis. 2006; 43:512-7; Chittick P et al. *J. Food Prot.* 2006; 69:1150-3), detection of a deliberate release is not easy and requires enhanced surveillance.

Heterologous Prime/Boost Immunization Regimens.

When critical antigens in different forms or via different routes are used to prime and boost, the breadth and magnitude of the immune response is increased. Heterologous prime/boost is a highly flexible strategy to enhance immunogenicity. The initial observations in mice involved enhancing immune responses to protein antigens (Vindurampulle C J et al., *Vaccine* 2004; 22:3744-50). Mucosal immunization with *S. Typhi* expressing fragment C of tetanus toxin primed mice to develop enhanced serum tetanus toxin neutralizing antibody titers when mice were subsequently inoculated parenterally with a single dose of tetanus toxoid (Id.). Similarly, non-human primates immunized mucosally (nasally) with *S. Typhi* expressing full length Protective Antigen (PA) of *Bacillus anthracis* mounted anamnestic serum antibody responses when immunized subsequently with a single dose of parenteral vaccine containing PA. Unconjugated pneumococcal, meningococcal and *S. Typhi* Vi polysaccharides that exist as licensed vaccines for adults and older children are not immunogenic in infants, and even in adults immune responses cannot be boosted and are relatively short-lived compared to protein antigens (Keitel W A et al., *Vaccine* 1994; 12:195-9). A clinical trial is currently underway addressing whether oral immunization of volunteers with CVD 909 (Wang J Y et al., *Infect. Immun.* 2000:4647-52; Tacket C D et al., *J. Infect. Dis.* 2004; 190:565-70), an attenuated *S. Typhi* vaccine strain that constitutively expresses Vi capsular polysaccharide can prime vaccines to mount enhance serum Vi antibody responses when subsequently immunized with parenteral Vi polysaccharide. We propose that mucosal administration with live attenuated NTS vaccines primes the immune system of animals to mount enhanced, broadened immune responses when they are subsequently given the homologous O:H glycoconjugate (i.e., OPS linked to Phase 1 flagellar protein) parenterally.

The present invention relates to appropriately engineered attenuated strains of *Salmonella enterica* serovars *Typhimurium* and *Enteritidis* and their use in vaccinating against these NTS serovars by: 1) allowing safer, high yield preparation of purified O polysaccharide (OPS) and flagella protein for making conjugate vaccines, and 2) by their use in a heterologous mucosal prime/parenteral boost immunization strategy in which subjects given the attenuated strains of *S. Typhimurium* and *S. Enteritidis* orally are subsequently boosted parenterally with conjugate vaccine comprising *Salmonella* Group B or D OPS covalently linked, respectively, to phase 1 flagella protein of *S. Typhimurium* and *S. Enteritidis*. The invention will markedly broaden the immune responses elicited and enhance antibodies and cell mediated immunity (CMI) stimulated by the live vaccine to synergize with the serum IgG anti-OPS bactericidal antibodies and anti-flagella antibodies stimulated by the parenteral conjugate vaccine. Since *S. Typhimurium* and *S. Enteritidis* are the most common NTS serovars associated with invasive and severe NTS clinical disease in the USA, and globally, the invention encompasses a rational, broad spectrum vaccine against NTS. It is contemplated that the bivalent vaccine will also cross protect against other Group B and D serovars. Addition of a group C1 or C2 conjugate is further contemplated. As such, coverage will be provided against virtually all NTS associated with invasive and severe NTS disease in the U.S. and worldwide.

SUMMARY OF THE INVENTION

According to non-limiting example embodiments, in one aspect, the present invention is directed to methods that include the production of well tolerated and immunogenic vaccine strains of *Salmonella Typhimurium* and *Salmonella Enteritidis.*

In another aspect, the invention is directed to a *Salmonella* serovar strain, wherein the strain has at least one attenuating mutation selected from group consisting of an attenuating mutation in the guaBA locus, the guaB gene, the guaA gene, the clpP gene, the clpX gene and the clpPX locus and said *Salmonella* serovar is selected from the group consisting of *Salmonella Typhimurium* (a serovar within serogroup B) and *Salmonella Enteritidis* (a serovar within serogroup D).

In another aspect, the present invention is directed to conjugate vaccines. In particular, the present invention encompasses a *Salmonella enterica* serovar conjugate vaccine comprising an O polysaccharide (OPS) conjugated to a flagellin protein or a fragment or a derivative thereof, such as a Phase 1 major flagella subunit protein (flagellin, the gene product encoded by fliC) from epidemiologically relevant serovars such as *S. Typhimurium* and *S. Enteritidis.*

In another aspect, the invention is directed to methods of inducing an immune response, comprising administering to a subject in need thereof an effective amount of a *Salmonella enterica* serovar conjugate vaccine comprising an O polysaccharide of serogroup B conjugated to Phase 1 (H:i) or Phase 2 (H:1,2) flagella protein of *S. Typhimurium* or O polysaccharide of group D conjugated to Phase 1 flagella of *S. Enteritidis* (H:g,m).

In some embodiments, the invention is directed to methods of inducing an immune response, comprising administering to a subject in need thereof a vaccine comprising an effective amount of genetically modified attenuated *Salmonella enterica* serovar selected from the group consisting of *S. Typhimurium* and *S. Enteritidis.*

In another aspect, the invention is directed to methods for preventing or attenuating an infection caused by *Salmonella*, comprising administering to a subject in need thereof a first vaccine comprising an effective amount of genetically modified attenuated *Salmonella enterica* serovar and a second vaccine comprising an effective amount of a conjugate comprising a homologous O polysaccharide (OPS) and a flagellin protein, such as a Phase 1 flagella protein or a fragment or a derivative thereof.

In another aspect, the invention is directed to a pharmaceutical formulation comprising one or more of the attenuated *Salmonella* strains of the present invention. In some embodiments of the invention, the formulations are oral pharmaceutical formulations.

In another aspect, attenuated *Salmonella Typhimurium* and *Salmonella Enteritidis* vaccine strains can be genetically modified to hyper-express Phase 1 flagella with the practical goal of enhancing yields of purified flagella protein which can be used as a carrier protein in conjugate vaccines.

DETAILED DESCRIPTION OF THE INVENTION

Conjugate Vaccines

Figure 1:
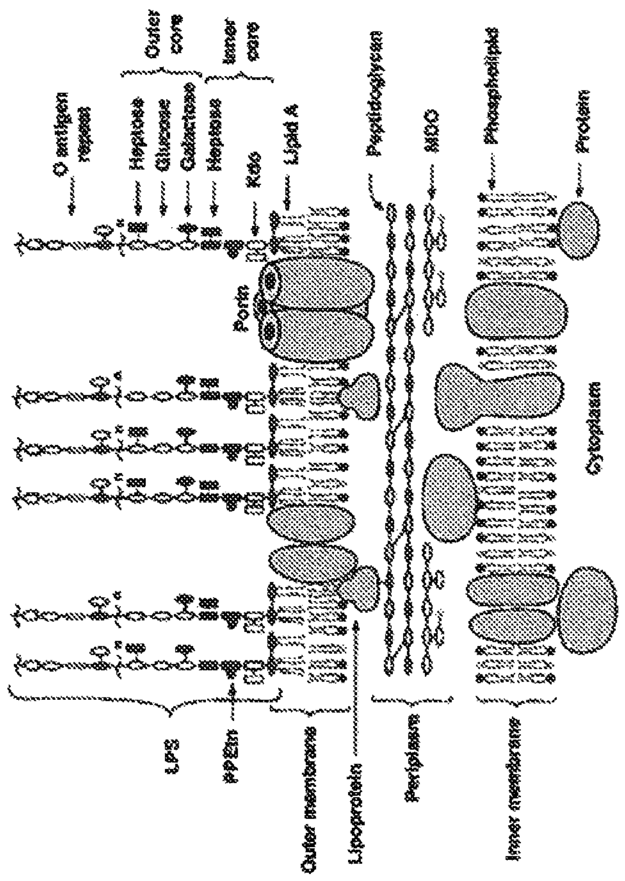
FIG. 1. Structure of the cell wall from a typical Gram-negative bacterium.

In one aspect, the present invention is directed to conjugate vaccines for *Salmonella*. In particular, the present invention encompasses *Salmonella* conjugate vaccines comprising an O-polysaccharide (OPS) conjugated to a flagellin protein. A conjugate vaccine comprising a flagellin protein comprises any known flagellin protein (see, for example, International Application PCT/US2004/034910 and U.S. 60/512,878, which are incorporated by reference in their entirety). In particular aspects of the invention, a flagellin protein is any known flagellin protein of *S. Typhimurium* or *S. Enteritidis*. In some embodiments of the invention, the flagellin protein is a phase 1 flagella protein (FliC).

As used herein, the term "phase 1 flagella" is intended to encompass: 1] flagella expressed from biphasic serovars such as *S. Typhimurium*, where both a phase 1 (FliC) and an additional phase 2 flagella (FljB) are expressed, and 2] flagella expressed by monophasic *Salmonella* serovars such as *S. Enteritidis*, which express only one type of flagella (FliC).

An OPS-flagella protein conjugate vaccine in which the OPS derives from epidemiologically relevant O serogroups such as serogroup B (which includes serovar *S. Typhimurium*) or serogroup D (which includes serovar *S. Enteritidis*).

The OPS and flagellin protein of the conjugated vaccine may be identical to a molecule which is characteristic of a *Salmonella* serovar, or they may be derivatives or fragments of such molecules. Preferably, the flagellin protein is from the same *Salmonella* serovar as the OPS. In some embodiments, the *Salmonella* serovar is selected from the group consisting of Group B and Group D serovars. In some embodiments, the OPS and flagellin protein are characteristic of *S. Typhimurium* (Group B). In some embodiments, the OPS and flagella protein are characteristic of *S. Enteritidis* (Group D). In some embodiments of the present invention, the conjugate vaccines provide more immunogenicity and protection than those OPS conjugated to standard carrier proteins (e.g., *Corynebacterium* diphtheria CRM).

In some embodiments, the conjugate vaccine comprises an OPS of serogroup B *Salmonella* (which includes serovar *S. Typhimurium*) covalently linked to the Phase 1 H:i flagella of serovar *S. Typhimurium*. This conjugate vaccine would also protect against an epidemiologically important variant of *S. Typhimurium*, serovar I 4,[5],12:i:-. clinically relevant level of cross protection might also be conferred against other epidemiologically important serovars within serogroup B such as *Salmonella* Heidelberg (antigenic formula 1,4,5,12:r:1,2), which is important in the USA, and *Salmonella* Stanleyville (antigenic formula 1,4,5,12:z4,z23:1,2), which is important in sub-Saharan Africa. The cross protection would be based on antibodies directed against shared O antigen 4, the immunodominant O antigen that defines serogroup B *Salmonella*.

In some embodiments, the conjugate vaccine for *S. Enteritidis* infections comprises an OPS of serogroup D (which includes serovar *S. Enteritidis*) covalently linked to the Phase 1 H:g,m flagella of serovar *S. Enteritidis*. This conjugate would be expected to provide cross protection against *Salmonella* Dublin (antigenic formula 1,9,12:g,p:-[Vi]), which is an epidemiologically important cause of invasive NTS disease in the USA and in some parts of sub-Saharan Africa (Levy H et al. *J Clin Microbiol* 2008; 46: 1861-1866; Tennant et al PLoS-NTD 2010; in press).

In some embodiments, the conjugate vaccines made from *S. Typhimurium* or *S. Enteritidis* are able to confer immunity against other *Salmonella* serovars. In some embodiments, immunity is conferred against S. Heidelberg (Group B, H:r) and S. Panama (Group D, H:l,v) serovars, which share O group but not Phase 1 H serotype antigens with *S. Typhimurium* and *S. Enteritidis*.

In some embodiments, the OPS and Phase 1 flagella protein are isolated from an attenuated *S. Typhimurium* (Group B) or *S. Enteritidis* (Group D) strain. In some embodiments, the OPS and Phase 1 flagella proteins are isolated from the genetically modified attenuated strains described herein. In some embodiments, the *S. Typhimurium* (Group B) or *S. Enteritidis* (Group D) has at least one attenuating mutation selected from group consisting of an attenuating mutation in the guaBA locus, the guaB gene, the guaA gene, the clpP gene, the clpX gene, and the clpPX locus. Combinations of attenuating mutations are further contemplated in accordance with the invention.

*Salmonella* serovars harboring a mutation in the clpP gene (that encodes a protease) are hyper-flagellated yet do not exhibit diminished bacterial cell growth at 30° or 37° C. Such serovars include, for example, *S. Typhimurium* (Tomoyasu T et al., *J. Bacteriol.* 2002; 184:645-53). Such strains could greatly enhance the yields of flagella protein during large-scale manufacture, and the use of such strains to produce conjugate vaccines is encompassed by the present invention.

In one embodiment, the immunogenicity of the conjugate vaccine is greater than the immunogenicity of at least one carrier alone. Methods of measuring immunogenicity are well known to those in the art and primarily include measurement of serum antibody including measurement of amount, avidity, and isotype distribution at various times after injection of the conjugate vaccine. Greater immunogenicity may be reflected by a higher titer and/or increased life span of the antibodies. Immunogenicity may also be measured by the ability to induce protection to challenge with noxious substances or virulent organisms. Immunogenicity may also be measured by the ability to immunize neonatal and/or immune deficient mice. Immunogenicity may be measured in the patient population to be treated or in a population that mimics the immune response of the patient population.

In some embodiments of the present invention, the OPS and their homologous flagellin, e.g, Phase 1 flagella protein, in accordance with the invention can include functional groups or, alternatively, can be chemically manipulated to bear functional groups. The presence of functional groups may facilitate covalent conjugation. Such functional groups include, but are not limited to, amino groups, carboxyl groups, aldehydes, hydrazides, epoxides, and thiols.

In one embodiment, the invention provides a conjugate vaccine capable of inducing an immune response, the vaccine comprising (a) an OPS of *S. Typhimurium* conjugated to (b) Phase 1 flagella protein of *S. Typhimurium* or a fragment or derivative thereof.

In another embodiment, the invention provides a conjugate vaccine capable of preventing or attenuating an infection caused by *Salmonella Enteritidis*, the vaccine comprising (a) an OPS of *S. Enteritidis* conjugated to (b) Phase 1 flagella protein of *S. Enteritidis* or a fragment or derivative thereof.

In some embodiments, fragments or derivatives of the Phase 1 flagella for use in the conjugate vaccine include any internal antigenic portion(s) of the Phase 1 flagella protein.

In some embodiments, the OPS is one which, when introduced into a mammal (either animal or human) elicits antibodies which are capable of reacting with the *Salmonella* from which the OPS is derived.

Examples of fragments or derivatives of the Phase 1 flagella protein include fragments of the natural protein, including internal sequence fragments of the protein that retain their ability to elicit protective antibodies against the *Salmonella* from which it is derived. The derivatives are also intended to include variants of the natural protein (such as proteins having changes in amino acid sequence but that retain the ability to elicit an immunogenic, biological, or antigenic property as exhibited by the natural molecule), for example, the variants of the Phase 1 flagella protein with an altered flanking sequence.

By derivative is further meant an amino acid sequence that is not identical to the wild type amino acid sequence, but rather contains at least one or more amino acid changes (deletion, substitutions, inversion, insertions, etc.) that do not essentially affect the immunogenicity or protective antibody responses induced by the modified protein as compared to a similar activity of the wild type amino acid sequence, when used for the desired purpose. In some embodiments, a derivative amino acid sequence contains at least 85-99% homology at the amino acid level to the specific amino acid sequence. In further embodiments, the derivative has at least 90% homology at the amino acid level, while in other embodiments, the derivative has at least 95% homology.

The Phase 1 flagella protein that is conjugated to the polysaccharide in the vaccine of the invention may be a peptide encoding the native amino acid sequence or it may be a derivative or fragment of the native amino acid sequence.

In some embodiments, Phase 1 flagella protein from other serovars of *Salmonella* may also be prepared and used in a similar manner as a slight variability in the sequence of the protein might not alter the biological properties and their functional ability to elicit protective antibodies against other serovars. In some embodiments, a conjugate vaccine comprising a Phase 1 flagella protein from a particular group B serovar can provide protection against other group B serovars, for example, in addition to protection against the group B serovar from which it was derived.

The peptides used in the invention, whether encoding a native protein or a derivative thereof, are conjugated to an OPS moiety by any means that retains the ability of these proteins to induce protective antibodies against *Salmonella.*

Heterogeneity in the vaccine may be provided by mixing specific conjugated species. For example, the vaccine preparation may contain one or more copies of one of the peptide forms conjugated to the carbohydrate, or the vaccine preparation may be prepared to contain more than one form of the above derivatives and/or the native sequence, each conjugated to a polysaccharide used therein.

A multivalent vaccine may also be prepared by mixing the OPS and Phase 1 flagella protein conjugates with other proteins, such as other *Salmonella* antigens, antigens against other organisms, diphtheria toxin or tetanus toxin, and/or other polysaccharides, using techniques known in the art. In some embodiments, the invention is directed to a multivalent vaccine comprising a mixture of conjugates derived from various *Salmonella* serovars, each conjugate comprising an OPS and Phase 1 flagella protein characteristic of the serovar.

In one embodiment, the *S. Enteritidis* or *S. Typhimurium* conjugate vaccines of the invention are combined with conjugate vaccines from *Salmonella* group C1 and/or group C2 serovars. In some embodiments, group C1 or C2 serovar conjugate vaccines can likewise comprise OPS and Phase 1 flagella proteins characteristic of the C1 or C2 serovars, and prepared in accordance with the invention.

As used herein, a polysaccharide or protein is "characteristic" of bacteria if it is substantially similar or identical in structure or sequence to a molecule naturally associated with the bacteria. The term is intended to include both molecules which are specific to the organism, as well as molecules which, though present on other organisms, are involved in the virulence or antigenicity of the bacteria in a human or animal host.

In some embodiments, the flagellin protein is isolated from genetically modified *Salmonella*. In some embodiments, the genetically modified *Salmonella* include *S. Typhimurium* or *S. Enteritidis* that harbor an attenuating mutation in clpP (that encodes a protease) that results in variants that are hyperflagellated yet do not exhibit diminished bacterial cell growth at 30° or 37° C. (Tomoyasu T et al., *J. Bacteriol.* 2002; 184:645-53). In some embodiments, use of such mutants greatly enhances the yields of flagella protein during large-scale manufacture. In some embodiments, the *S. Typhimurium* or *S. Enteritidis* cells are engineered to overexpress FliC Phase 1 flagella monomers (FliC). In some embodiments, fliD will also be deleted, leading to secretions of non-polymerized extracellular FliC monomers. In some embodiments, the fljB gene of *S. Typhimurium* is also deleted, which encodes an alternate phase 2 flagellin not required for the conjugate vaccine.

In some embodiments, the *S. Typhimurium* or *S. Enteritidis* cells are modified to harbor multiple gene copies to overexpress Phase 1 flagella protein. In some embodiments, the Phase 1 flagella protein is recombinantly produced, for example, in *E. coli.*

Methods of Making the Conjugate Vaccine

Preparation of purified protein from flagella structures on bacterial cells, or secreted flagellin protein, including but not limited to homologous and heterologous *Salmonella* strains, expressing the desired flagellin protein, or bacterial expression system such as *E. coli*, for use in conjugation can be accomplished through several methodologies, including but not limited to, mechanical shearing, removal at low pH, heating or purification from bacterial supernatants. Mechanical shearing has been shown to be effective in preparation of flagellin protein suitable for conjugation to OPS.

Figure 8:
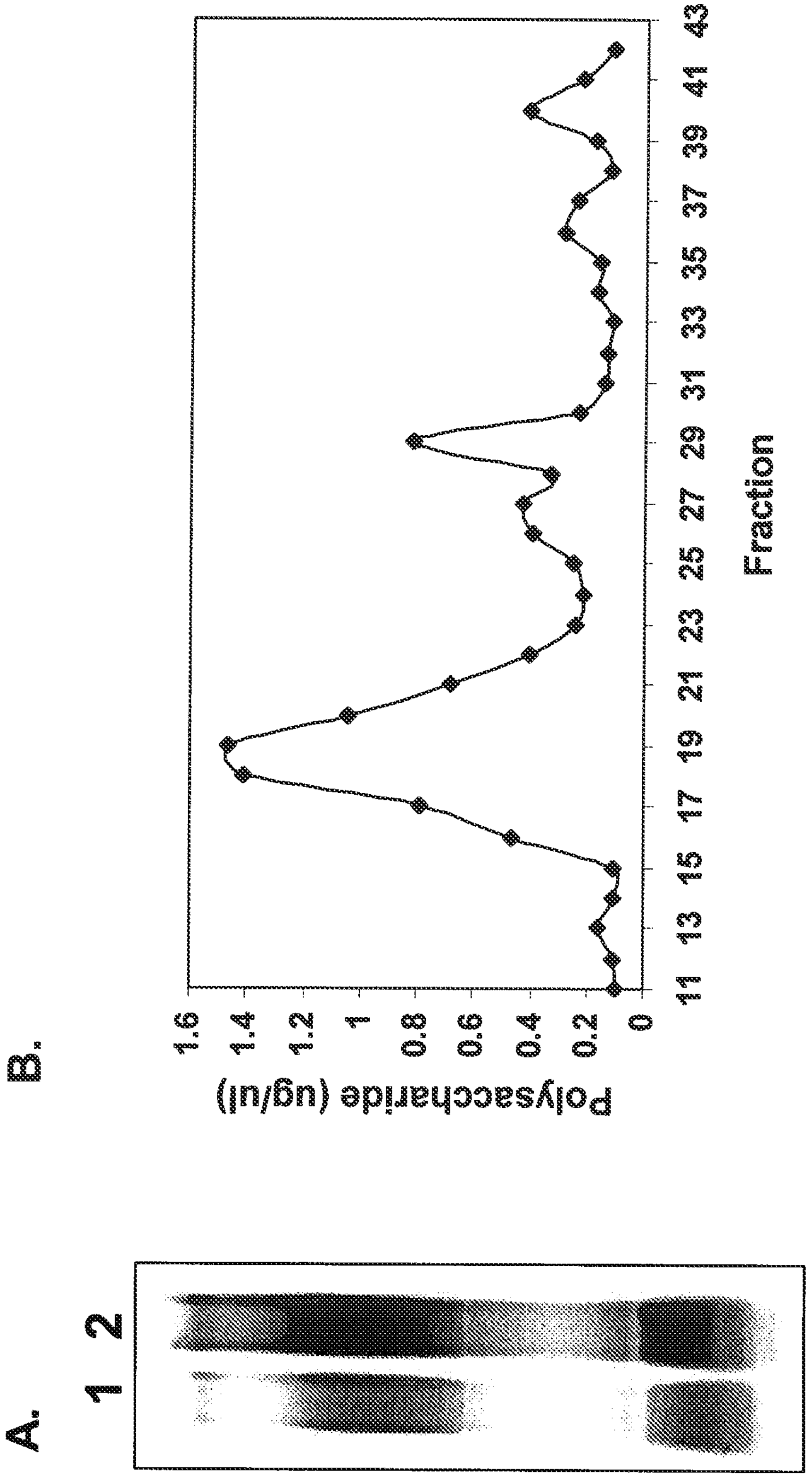
FIG. 8. Purification of *Salmonella* Lipopolysaccharide. (A) Emerald Green stained SDS-PAGE pattern of *S. Enteritidis* LPS. Lane: 1, 37.5 ug; 2, 70 ug. (B) Size exclusion gel filtration profile of *S. Enteritidis* OPS through a Superdex 70 sepharose column in PBS. High molecular weight OPS fractions are designated 16-22. Polysaccharide concentrations were assessed by resorcinol assay, using the homologous LPS as a standard.
Figure 9:
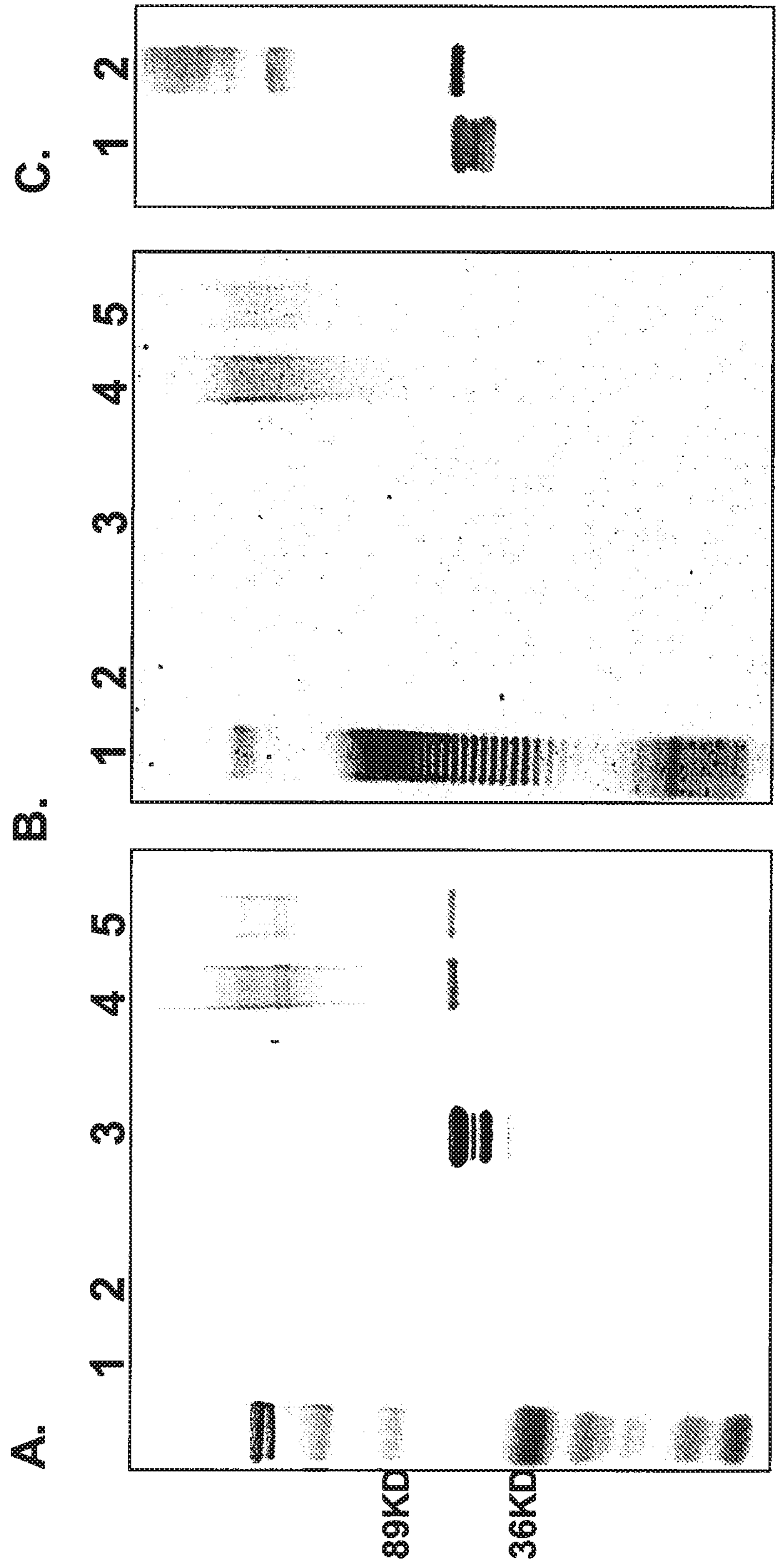
FIG. 9. Conjugation of *Salmonella* Outer Membrane Polysaccharide to Flagellin monomers. 4-20% SDS-Gel followed by Coomasie (A) or Emerald Green (B) staining Lane: 1, 10 ug LPS; 2, 6 ug HMW-OPS; 3, 6 ug de-polymerized flagella; 4, 6 ug protein as conjugate to HMW-OPS; 5, 3 ug protein as conjugate to HMW-OPS. (C) Western Blot analysis for flagellin. Lane: 1, 0.4 ug depolymerized flagella; 2, 0.4 ug protein as conjugate to HMW-OPS.

Purification of OPS can be accomplished by methods including by not limited to mild acid hydrolysis removal of lipid A from LPS, as this has been shown to preserve the O-acetyl groups that are important for immunogenicity. Other embodiments may include hydrazine as an agent for OPS preparation. Preparation of LPS can be accomplished by methods including but not limited to those of Darveau, R. P., and Hancock, R. E. W. 1983. *J. Bacteriol.*, 155(2):831-838, or Westphal, O. and Jann, K. 1965. Methods in Carbohydrate Chemistry. 5:83-91 as are incorporated by reference herein. As is shown in FIGS. 8 and 9, LPS was purified by a modification of the methods of Darveau and Hancock, followed by mild acid hydrolysis to remove lipid A and liberate free Core/KDO linked OPS. Conjugation of OPS of *S. Typhimurium* or *S. Enteritidis* and a flagellin protein of the same serovar can be carried out by methods as described in, for example, US Patent Application Publication No. 20090028889. Techniques to conjugate OPS and the Phase 1 flagella protein include, in part, coupling through available functional groups (such as amino, carboxyl, thio and aldehyde groups). See, e.g., Hermanson, Bioconjugate Techniques (Academic Press; 1992); Aslam and Dent, eds. Bioconjugation: Protein coupling Techniques for the Biomedical Sciences (MacMillan: 1998); S. S. Wong, *Chemistry of Protein Conjugate and Crosslinking CRC Press* (1991), and Brenkeley et al., Brief Survey of Methods for Preparing Protein Conjugates With Dyes, Haptens and Cross-Linking Agents, *Bioconjugate Chemistry* 3 #1 (January 1992); Jacob, C. O, et al., *Eur. J. Immunol.* 16:1057-1062 (1986); Parker, J. M. R. et al., In: *Modern Approaches to Vaccines*, Chanock, R. M. et al., eds, pp. 133-138, Cold Spring Harbor Laboratory, Cold Spring Harbor, N.Y. (1983); Zurawski, V. R, et al., *J. Immunol.* 121:122-129 (1978); Klipstein, F. A, et al., *Infect. Immun.* 37:550-557 (1982); Bessler, W. G, *Immunobiol.* 170:239-244 (1985); Posnett, D. N, et al., *J. Biol. Chem.* 263:1719-1725 (1988); Ghose, A. C, et al., *Molec. Immunol.* 25:223-230 (1988); all of which disclosures are incorporated herein by reference). An example of a conjugate vaccine was developed against *Haemophilus influenzae* (Anderson, P, Infec. and *Immunology* 39:223-238 (1983); Chu, C, et al., *Infect. Immun.* 40:245-256 (1983); Lepow, M, *Pediat. Infect. Dis. J.* 6:804-807 (1987), which disclosures are incorporated herein by reference), and this model may be employed in constructing the novel vaccines of the present invention. Additional methods for producing such a conjugate vaccine are disclosed by European Patent Publication 245,045; U.S. Pat. Nos. 4,673,574 and 4,761,283; U.S. Pat. No. 4,789,735; European Patent Publication No. 206,852; U.S. Pat. No. 4,619,828; U.S. Pat. No. 4,284,537; U.S. Pat. No. 5,192,540; U.S. Pat. No. 5,370,872; U.S. Pat. No. 5,302,386; and U.S. Pat. No. 5,576,002 all of which disclosures are incorporated herein by reference.

For example, in the case of carbohydrate or lipid conjugation, functional amino and sulfhydryl groups may be incorporated therein by conventional chemistry. For instance, primary amino groups may be incorporated by reaction with ethylenediamine in the presence of sodium cyanoborohydride and sulfhydryls may be introduced by reaction of cysteamin dihydrochloride followed by reduction with a standard disulfide reducing agent.

Heterobifunctional crosslinkers, such as, for example, sulfosuccinimidyl (4-iodoacetyl)aminobenzoate, which link the epsilon amino group on the D-lysine residues of copolymers of D-lysine and D-glutamate to a sulfhydryl side chain from an amino terminal cysteine residue on the peptide to be coupled, may be used to increase the ratio of OPS to a flagellin protein and/or a flagellin protein to OPS in the conjugate.

Flagellin protein may contain amino acid side chains such as amino, carbonyl, hydroxyl, or sulfhydryl groups or aromatic rings that can serve as sites for conjugation. Residues that have such functional groups may be added to either OPS or to a flagellin protein. Such residues may be incorporated by solid phase synthesis techniques or recombinant techniques, both of which are well known in the art.

OPS and a flagellin protein may be chemically conjugated using conventional crosslinking agents such as carbodiimides. Examples of carbodiimides are 1-cyclohexyl-3-(2-morpholinyl-(4-ethyl)carbodiimide (CMC), 1-ethyl-3-(3-dimethylaminopropyl)carbodiimide (EDC), and 1-ethyl-3-(4-azonia-44-dimethylpentyl)carbodiimide.

Examples of other suitable crosslinking agents are cyanogen bromide, glutaraldehyde and succinic anhydride. In general, any of a number of homobifunctional agents including a homobifunctional aldehyde, a homobifunctional epoxide, a homobifunctional imidoester, a homobifunctional N-hydroxysuccinimide ester, a homobifunctional maleimide, a homobifunctional alkyl halide, a homobifunctional pyridyl disulfide, a homobifunctional aryl halide, a homobifunctional hydrazide, a homobifunctional diazonium derivative or a homobifunctional photoreactive compound may be used. Also included are heterobifunctional compounds, for example, compounds having an amine-reactive and a sulfhydryl-reactive group, compounds with an amine-reactive and a photoreactive group, and compounds with a carbonyl-reactive and a sulfhydryl-reactive group.

Specific examples of homobifunctional crosslinking agents include the bifunctional N-hydroxysuccinimide esters dithiobis(succinimidylpropionate), disuccinimidyl suberate, and disuccinimidyl tartarate; the bifunctional imidoesters dimethyl adipimidate, dimethyl pimelimidate, and dimethyl suberimidate; the bifunctional sulfhydryl-reactive crosslinkers 1,4-di-[3'-(2'-pyridyldithio)propionamido]butane, bismaleimidohexane, and bis-N-maleimido-1,8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamide) ethyl]disulfide; the bifunctional aldehydes formaldehyde, malondialdehyde, succinaldehyde, glutaraldehyde, and adiphaldehyde; a bifunctional epoxied such as 1,4-butaneodiol diglycidyl ether; the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N1N'-ethylene-bis(iodoacetamide), N1N'-hexamethylene-bis(iodoacetamide), N1N'-undecamethylene-bis(iodoacetamide), as well as benzylhalides and halomustards, such as ala'-diiodo-p-xylene sulfonic acid and tri(2-chloroethyl)amine, respectively.

Examples of other common heterobifunctional crosslinking agents that may be used include, but are not limited to, SMCC (succinimidyl-4-(N-maleimidomethyl)cyclohexane-1-carboxylate), MBS (m-maleimidobenzoyl-N-hydroxysuccinimide ester), SIAB (N-succinimidyl(4-iodacteyl)aminobenzoate), SMPB (succinimidyl-4-(p-maleimidophenyl) butyrate), GMBS (N-(-maleimidobutyryloxy)succinimide ester), MPHB (4-(4-N-maleimidophenyl)butyric acid hydrazide), M2C2H (4-(N-maleimidomethyl)cyclohexane-1-carboxyl-hydrazide), SMPT (succinimidyloxycarbonyl-a-methyl-a-(2-pyridyldithio)toluene), and SPDP (N-succinimidyl 3-(2-pyridyldithio)propionate). For example, crosslinking may be accomplished by coupling a carbonyl group to an amine group or to a hydrazide group by reductive amination.

In another aspect of the invention, OPS and a flagellin protein are conjugated through polymers, such as PEG, poly-D-lysine, polyvinyl alcohol, polyvinylpyrollidone, immunoglobulins, and copolymers of D-lysine and D-glutamic acid. Conjugation of OPS to a flagellin protein may be achieved in any number of ways, including involving one or more crosslinking agents and functional groups on the OPS and/or a flagellin protein. The polymer may be derivatized to contain functional groups if it does not already possess appropriate functional groups.

In some embodiments, 1-cyano-4-dimethylaminopyridinium tetrafluoroborate (CDAP) conjugation chemistry is used to achieve efficient synthesis of group-specific OPS-FliC conjugates (see e.g. Lees A. et al. 1996. *Vaccine.* 14(3): 190-198, and Shafer D E et al. *Vaccine.* 2000. 18(13):1273-81 as is incorporated by reference herein). As shown in FIG. 9, activation and derivitization of OPS with CDAP chemistry, followed by direct coupling to flagellin protein has been demonstrated to be effective as a method of conjugation.

In some embodiments, the OPS or Phase 1 flagella protein is conjugated to a linker prior to conjugation. In some embodiments, the linker is adipic acid dihydrazide (ADH). The present invention contemplates the use of any linker capable of conjugating OPS to a Phase 1 flagella protein. In some embodiments, the presence of a linker promotes optimum immunogenicity of the conjugate and more efficient coupling. In some embodiments, the linkers separate the two antigenic components by chains whose length and flexibility can be adjusted as desired. Between the bifunctional sites, the chains can contain a variety of structural features, including heteroatoms and cleavage sites. In some embodiments, linkers also permit corresponding increases in translational and rotational characteristics of the antigens, increasing access of the binding sites to soluble antibodies. Besides ADH, suitable linkers include, for example, heterodifunctional linkers such as ε-aminohexanoic acid, chlorohexanol dimethyl acetal, D-glucuronolactone and p-nitrophenyl amine. Coupling reagents contemplated for use in the present invention include hydroxysuccinimides and carbodiimides. Many other linkers and coupling reagents known to those of ordinary skill in the art are also suitable for use in the invention. Such compounds are discussed in detail by Dick et al., Conjugate Vaccines, J. M. Cruse and R. E. Lewis, Jr., eds., Karger, New York, pp. 48-114, hereby incorporated by reference.

In some embodiments, ADH is used as the linker. In some embodiments, the molar ratio of ADH to OPS in the reaction mixture is typically between about 10:1 and about 250:1. In some embodiments, a molar excess of ADH is used to ensure more efficient coupling and to limit OPS-OPS coupling. In some embodiments, the molar ratio is between about 50:1 and about 150:1. In other embodiments, the molar ratio is about 100:1. Similar ratios of AH-OPS to the Phase I flagella protein in the reaction mixture are also contemplated. In some embodiments, one ADH per OPS is present in the AH-OPS conjugate.

Other linkers are available and can be used to link two aldehyde moieties, two carboxylic acid moieties, or mixtures thereof. Such linkers include ($C_1$-$C_6$) alkylene dihydrazides, ($C_1$-$C_6$) alkylene or arylene diamines, -aminoalkanoic acids, alkylene diols or oxyalkene diols or dithiols, cyclic amides and anhydrides and the like. For examples, see U.S. Pat. No. 5,739,313.

In accordance with the invention, a variety of methods known to those skilled in the art can be employed to make the conjugate vaccines. For example, any suitable functionalization reaction can be employed to activate the Phase 1 flagella protein with hydrazide groups. Conventional methods for preparing hydrazide-modified proteins include EDC (1-[3-(dimethylamino)propyl]-3-ethyl carbodiimide hydrochloride) catalysis and a two-step process using N-succinimidyl iodoacetate and thiol hydrazide through lysine ϵ-amino groups of the protein. See, e.g., King et al., *Biochemistry* 1986; 25:5774-5779. In some embodiments, the modified protein prepared by EDC catalysis is fractionated in order for it to be suitable for use in conjugation. In some embodiments, hydrazide groups are introduced into proteins through the carboxyl groups of aspartic acid and glutamic acid residues on the protein using a carbodiimide reaction, for example, by reaction with hydrazine, carbohydrazide, succinyl dihydrazide, adipic acid dihydrazide or any other dihydrazides in the presence of EDC. In some embodiments, ADH can be conjugated to CNBr activated OPS, followed by conjugation to flagellin protein through EDC mediated condensation onto carboxylic acid groups including but not limited to, glutamic acid and aspartic acid side chains. EDC is employed as a catalyst to activate and modify the protein reactant with hydrazine or the dihydrazide. Any water-soluble carbodiimide including EDC can be used as a catalyst. Under certain conditions, EDC-catalyzed proteins generally have a tendency to polymerize and precipitate. See Schneerson et al., *Infect. Immun.* 1986, 52:519-528; Shafer et al., Vaccine 2000; 18(13): 1273-1281; and Inman et al., *Biochemistry* 1969; 8:4074-4082. Aggregation and precipitation of the activated protein depends, in part, on its pH environment. Accordingly, the tendency to polymerize and precipitate can be controlled by maintaining such hydrazide-modified proteins soluble in a buffered solution. By buffer-exchanging the reaction mixture so as to maintain the activated protein at a pH of about 10.5, the activated protein remains soluble and stable for conjugation. Any suitable buffer can be employed. In some embodiments, a weak buffer such as $Na_2CO_3$ at a low concentration of from about 3 mM to about 10 mM is employed.

In some embodiments, the buffered hydrazide-modified protein can then be employed in preparing protein-polysaccharide conjugates without precipitation when added to activated polysaccharide at a pH of from about 6 to 8.5, or from about 6.5 to about 8. Any suitable functionalization reaction can be employed to activate the protein with aldehyde groups. In some embodiments, the protein is reacted with 1-amino-2,3-propanediol in the presence of EDC. Amino sugars such as glucosamine, galactosamine, and the like can be used in place of 1-amino-2,3-propanediol. In this reaction, EDC is also employed as a catalyst to activate and modify the protein reactant with the aminodiol through the carboxyl groups of aspartic acid and glutamic acid residues of the protein.

In some embodiments, conjugates can be prepared via the reaction of aldehyde and hydrazide groups (reductive amination). The reductive amination conjugation reaction can be employed to conjugate a hydrazide-modified reactant (protein or polysaccharide) or unmodified protein through available amino groups including but not limited to lysine side chains, to the other component containing aldehyde groups. In some embodiments, the reductive amination conjugation reaction proceeds without the aid of sodium cyanoborohydride because of the high efficiency of the hydrazide-aldehyde reaction. In some embodiments, at the end of the reductive amination conjugation reaction, sodium borohydride or another suitable reactant is employed to reduce the C═N double bond to a C—N single bond, as well as to reduce any residual aldehyde groups to alcohol groups. The reductive amination conjugation reaction in some embodiments avoids contamination of the resulting conjugate with cyanide, a by-product of sodium cyanoborohydride.

In some embodiments, during the conjugation process, the activated protein is in the form of a weakly buffered solution with a low buffer concentration of from about 3 mM to about 10 mM which is added to a strongly buffered (at pH of from about 6.5 to about 7.5, with a high buffer concentration of from about 100 mM to about 200 mM) activated polysaccharide solution. In some embodiments, the pH of the activated protein solution is buffered to from about 10 pH to about 11.5 pH, or in some embodiments to about 10.5 pH. In some embodiments, the activated polysaccharide solution is strongly buffered to from about 6 pH to about 8 pH, or from about 6.5 pH to about 7.5 pH. The hydrazide-aldehyde reductive amination reaction proceeds at a fast rate, and the precipitating effect of a pH lower than 10.5 (for example, a pH as low as from about 8.5 to about 9.5) on activated protein is overcome by the molecular properties of the reacting activated polysaccharide.

In some embodiments, the vaccine conjugates of the invention can be prepared via the reaction of hydrazide and cyanate groups (cyanalation conjugation). The cyanalation conjugation reaction is efficient and reversible, favoring the product formation. In certain embodiments, blocking agents are employed to remove residual cyanate groups. However, in other embodiments, addition of a blocking agent to the reaction mixture drives the conjugation reaction backward and reduces the conjugation yield. In some embodiments it can be desirable to employ blocking agents to quench the leftover residual cyanate groups, while in other embodiments their use is avoided. To remove residual cyanate groups in the conjugation product without using a blocking agent, the conjugation time can be prolonged.

In some embodiments of the invention, conjugation of OPS to flagellin is performed through activation of both OPS and flagellin. Activation of OPS can be accomplished by addition of carbonyldiimidazole to OPS in the presence of N,N-dimethylformamide and tetrabutylammonium, followed by reaction with butyldiamine to form carbamate, and subsequent bromoacetylation to yield activated OPS. Activation of Flagellin can be achieved by reaction with N-acetylhomocysteine. Conjugation of activated OPS and flagellin molecules following this scheme can be accomplished by mixing at pH 8.

In some embodiments, conjugation is conducted at a temperature of from about 0° C. to about 5° C. for about 36 to about 48 hours. In one embodiment, conjugation is conducted at about 4° C. for about 36 hours, followed by about an additional 18 to 24 hours at a temperature of from about 20°

C. to about 25° C. In another embodiment, conjugation is conducted for about 18 hours at about 20 to 24° C., such that the residual cyanate groups react with water and decompose. Longer or shorter conjugation times and/or higher or lower conjugation temperatures can be employed, as desired. In some embodiments, it is desirable, however, to conduct the conjugation reaction, at least initially, at low temperatures, for example, from about 0° C. to about 5° C., such as about 4° C., so as to reduce the degree of precipitation of the conjugate.

In some embodiments of the invention, conjugation of OPS to flagellin protein is on the terminal amino group of lysine residues. In some embodiments of the invention, conjugation is to cysteine groups. In some embodiments of the invention of conjugation of the OPS is to N-terminal Serine groups. In some embodiments of the invention, conjugation of OPS to flagellin is directed towards the C-terminal carboxylic acid group. In some embodiments of the invention, conjugation is to naturally occurring amino acid groups. In other embodiments of the invention, conjugation is to engineered amino acid sequences and residues within the flagellin protein.

In some embodiments of the invention, conjugation of flagellin to OPS is on random free hydroxyl groups on the OPS polysaccharide chain. In some embodiments of the invention, conjugation of flagellin to OPS is at the terminal end of the polysaccharide chain.

In some embodiments of the invention, the OPS and Phase 1 flagella protein reactants contain multiple reactive groups per molecule. In some embodiments, an activated OPS molecule can react with and form more than one linkage to more than one activated Phase 1 flagella protein molecule. Likewise, an activated Phase 1 flagella protein molecule can react with and form more than one linkage to more than one activated OPS molecule. Therefore, in some embodiments, the conjugate product is a mixture of various cross-linked matrix-type lattice structures. For example, a single linkage can be present, or 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more linkages can be present. The average number of linkages between an OPS and a Phase 1 flagella protein can be adjusted, as desired. In some embodiments, the average number of linkages can depend upon the type of OPS polysaccharide, the type of Phase I flagella protein, the conjugation method, the reaction conditions, and the like. In some embodiments, an average of 1 linkage to about 2, 3, 4, or 5 linkages is present, so as to avoid interfering with the ability of the FliC protein to stimulate the innate immune system via TLR5 by over-conjugation, and so as to not cause changes in the polysaccharide structure. However, in certain embodiments more than 5 linkages can be tolerated.

Figure 10:
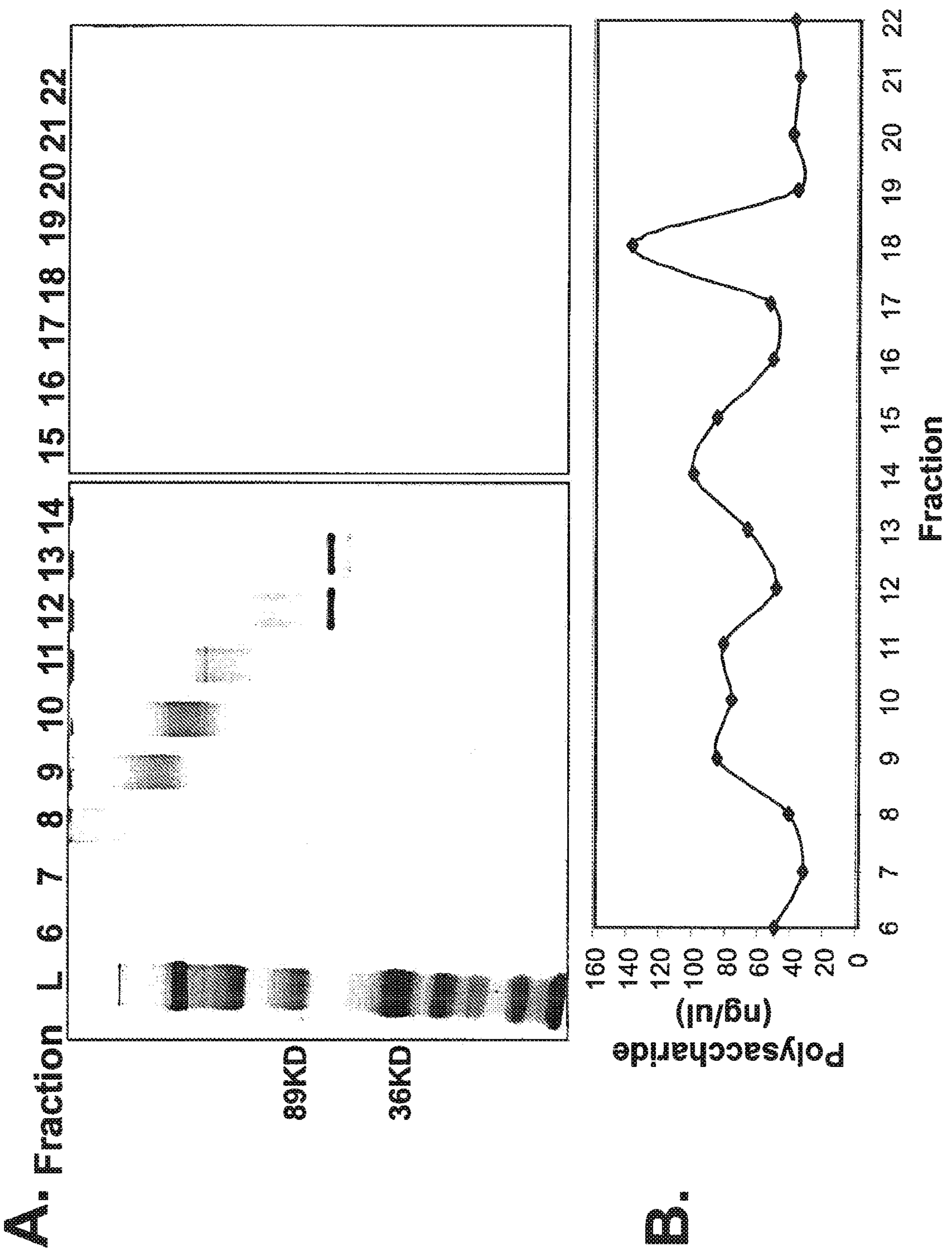
FIG. 10. Purification of Flagellin-OPS Conjugates. Gel filtration pattern of Flagella-HMW-OPS conjugates through a Superdex 700 size exclusion column. (A) Fractions were analyzed by SDS-PAGE with staining with Coomasie dye for protein. (B) Polysaccharide content in each fraction.

In some embodiments, purification processes such as column chromatography and/or ammonium sulfate precipitation of the conjugate from unconjugated polysaccharide may not be necessary. However, in certain embodiments it can be desirable to conduct one or more purification steps. In some embodiments, after conjugation, the conjugate can be purified by any suitable method. Purification is employed to remove unreacted polysaccharide, protein, or small molecule reaction byproducts. Purification methods include ultrafiltration, size exclusion chromatography, density gradient centrifugation, hydrophobic interaction chromatography, ammonium sulfate fractionation, ion exchange chromatography, ligand exchange chromatography, immuno-affinity chromatography, polymyxin-b chromatography, and the like, as are known in the art. In some embodiments, the conjugation reactions proceed with higher yield, and generate fewer undesirable small molecule reaction byproducts. Accordingly, in some embodiments no purification may be necessary, or only a minor degree of purification can be desirable. The conjugate can be concentrated or diluted, or processed into any suitable form for use in pharmaceutical compositions, as desired. Purification of OPS-flagellin conjugates has been demonstrated with the use of size exclusion chromatography (FIG. 10).

There are many coupling methods which can be envisioned for OPS-Phase 1 flagella protein conjugates. Other methods well known in the art for effecting conjugation of oligosaccharides to immunogenic carrier proteins are also within the scope of the invention. Such methods are described in, for example, U.S. Pat. Nos. 5,153,312 and 5,204,098; EP 0 497 525; and EP 0 245 045, the entire disclosures of which are hereby incorporated by reference.

Pharmaceutical Compositions of the Conjugate Vaccine

As would be understood by one of ordinary skill in the art, when the conjugate vaccine of the present invention is provided to an individual, it may be in a composition which may contain salts, buffers, adjuvants, or other substances which are desirable for improving the efficacy of the composition. Adjuvants are substances that can be used to specifically augment a specific immune response. Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, $AlK(SO_4)_2$, $AlNa(SO_4)_2$, $AlNH_4(SO_4)$, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus *Brucella*. Adjuvants are described by Warren et al. (*Ann. Rev. Biochem.*, 4:369-388, 1986), the entire disclosure of which is hereby incorporated by reference. Bacterial flagellin and flagellin fusion proteins have been demonstrated previously to be a potent adjuvant in mice and non-human primates (Mizel et al. 2009. *Clinical and Vaccine Immunology.* 16(1):21-28; McSorley et al. 2002. *The Journal of Immunology.* 169:3914-3919; Huleat et al. 2008. *Vaccine.* 26(2):201-214).

In some embodiments of the invention the use of flagellin protein as a carrier for OPS conjugate provides an inherent adjuvant boost, and stimulates a robust immune response without the addition of further adjuvant. Thus, in some embodiments, the flagellin protein acts an adjuvant which stimulates innate immunity through TLR5 to improve the immunogenicity of OPS within the conjugate vaccine.

In other embodiments, conventional adjuvants can be administered. Among those substances particularly useful as adjuvants are the saponins such as, for example, Quil A. (Superfos A/S, Denmark). In some embodiments, immunogenicity of the conjugates in both mice and rabbits is enhanced by the use of monophosphoryl lipid A plus trehalose dimycolate (Ribi-700; Ribi Immunochemical Research, Hamilton, Mont.) as an adjuvant. Examples of materials suitable for use in vaccine compositions are provided in *Remington's Pharmaceutical Sciences* (Osol, A, Ed, Mack Publishing Co, Easton, Pa., pp. 1324-1341 (1980), which disclosure is incorporated herein by reference).

The conjugate vaccines can be formulated into liquid preparations for, e.g., nasal, rectal, buccal, vaginal, peroral, intragastric, mucosal, perlinqual, alveolar, gingival, olfactory, or respiratory mucosa administration. Suitable forms for such administration include solutions, suspensions, emulsions, syrups, and elixirs. The conjugate vaccines can also be formulated for parenteral, subcutaneous, intradermal, intramuscular, intraperitoneal or intravenous administration, injectable administration, sustained release from implants, or administration by eye drops. Suitable forms for such administration include sterile suspensions and emulsions. Such conjugate vaccines can be in admixture with a suitable carrier, diluent, or excipient such as sterile water, physiological saline, glucose, and the like. The conjugate vaccines can also be lyophilized. The conjugate vaccines can contain auxiliary substances such as wetting or emulsifying agents, pH buffering agents, gelling or viscosity enhancing additives, preservatives, flavoring agents, colors, and the like, depending upon the route of administration and the preparation desired. Texts, such as *Remington: The Science and Practice of Pharmacy*, Lippincott Williams & Wilkins; 20th edition (Jun. 1, 2003) and *Remington's Pharmaceutical Sciences*, Mack Pub. Co.; $18^{th}$ and $19^{th}$ editions (December 1985, and June 1990, respectively), incorporated herein by reference in their entirety, can be consulted to prepare suitable preparations. Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

In some embodiments, the conjugate vaccine of the invention is administered parenterally. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In some embodiments, the OPS-Phase 1 flagella protein conjugates for parenteral administration may be in the form of a sterile injectable preparation, such as a sterile injectable aqueous or nonaqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Suspensions may be formulated according to methods well known in the art using suitable dispersing or wetting agents and suspending agents. The sterile injectable preparation may also be a sterile injectable solution or suspension in a parenterally acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid may likewise be used in the preparation of injectable preparations.

Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

In some embodiments, the conjugate vaccines are provided as liquid suspensions or as freeze-dried products. Suitable liquid preparations include, e.g., isotonic aqueous solutions, suspensions, emulsions, or viscous compositions that are buffered to a selected pH. Transdermal preparations include lotions, gels, sprays, ointments or other suitable techniques. If nasal or respiratory (mucosal) administration is desired (e.g., aerosol inhalation or insufflation), compositions can be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size, as discussed below.

When in the form of solutions, suspensions and gels, in some embodiments, the formulations of the conjugate contain a major amount of water (preferably purified water) in addition to the active ingredient. Minor amounts of other ingredients such as pH adjusters, emulsifiers, dispersing agents, buffering agents, preservatives, wetting agents, jelling agents, colors, and the like can also be present.

In some embodiments, the compositions are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. In some embodiments of the invention, phosphate buffered saline is used for suspension.

In some embodiments, the viscosity of the compositions can be maintained at the selected level using a pharmaceutically acceptable thickening agent. In some embodiments, methylcellulose is used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. In some embodiments, viscous compositions are prepared from solutions by the addition of such thickening agents.

In some embodiments, a pharmaceutically acceptable preservative can be employed to increase the shelf life of the compositions. Benzyl alcohol can be suitable, although a variety of preservatives including, for example, parabens, thimerosal, chlorobutanol, or benzalkonium chloride can also be employed. A suitable concentration of the preservative can be from 0.02% to 2% based on the total weight although there can be appreciable variation depending upon the agent selected.

In some embodiments, pulmonary delivery of the conjugate can also be employed. In some embodiments, the conjugate is delivered to the lungs of a mammal while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of the conjugate. Typically, each formulation is specific to the type of device employed and can involve the use of an appropriate propellant material, in addition to diluents, adjuvants and/or carriers useful in therapy.

In embodiments where the conjugate is prepared for pulmonary delivery in particulate form, it has an average particle size of from 0.1 μm or less to 10 μm or more. In some embodiments, it has an average particle size of from about 0.2, 0.3, 0.4, 0.5, 0.6, 0.7, 0.8, or 0.9 μm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 μm for pulmonary delivery. Pharmaceutically acceptable carriers for pulmonary delivery of the conjugates include carbohydrates such as trehalose, mannitol, xylitol, sucrose, lactose, and sorbitol. Other ingredients for use in formulations can include DPPC, DOPE, DSPC and DOPC. Natural or synthetic surfactants can be used, including polyethylene glycol and dextrans, such as cyclodextran and other related enhancers, as well as cellulose and cellulose derivatives, and amino acids can also be used. Liposomes, microcapsules, microspheres, inclusion complexes, and other types of carriers can also be employed.

Formulations suitable for use with a nebulizer, either jet or ultrasonic, typically comprise the conjugate dissolved or suspended in water at a concentration of about 0.01 or less to 100 mg or more of conjugate per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg of conjugate per mL of solution. The formulation can also include a buffer and a simple sugar (e.g., for protein stabilization and regulation of osmotic pressure). The nebulizer formulation can also contain a surfactant, to reduce or prevent surface induced aggregation of the conjugate caused by atomization of the solution in forming the aerosol.

Formulations for use with a metered-dose inhaler device generally comprise a finely divided powder containing the inventive compound suspended in a propellant with the aid of a surfactant. The propellant can include conventional propellants, such chlorofluorocarbon, a hydrochlorofluorocarbons, hydrofluorocarbons, and hydrocarbons, such as trichlorofluoromethane, dichlorodifluoromethane, dichlorotetrafluoroethanol, and 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing the conjugate, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

Attenuated *Salmonella* Strains

The present invention further relates to an attenuated *S. Enteritidis* or *S. Typhimurium* strain. In some embodiments, the attenuated strains may be used to induce an immune response in a subject without causing disease in the subject.

In some embodiments, *S. Enteritidis* strain R11 and *S. Typhimurium* strain 177 are used as starting material strains. The *S. Enteritidis* or *S. Typhimurium* strains of the present invention are attenuated. As used herein, attenuated strains are those that have a reduced, decreased, or suppressed ability to cause disease in a subject, or those completely lacking in the ability to cause disease in a subject. Attenuated strains may exhibit reduced or no expression of one or more genes, may express one or more proteins with reduced or no activity, may exhibit a reduced ability to grow and divide, or a combination of two or more of these characteristics. The attenuated strains of the present invention may be living or dead.

In some embodiments, the attenuated *S. Enteritidis* or *S. Typhimurium* strains of the present invention have a mutation in one or more of the guaBA locus, the guaB gene, the guaA gene, the clpP gene, the clpX gene and the clpPX locus. For example, the attenuated *S. Enteritidis* and *S. Typhimurium* strains of the present invention may have a mutation (i) in the guaB gene and the clpP gene, (ii) in the guaA gene and the clpP gene, (iii) in the guaBA locus, and the clpP gene, (iv) in the guaB gene and the clpX gene, (v) in the guaA gene and the clpX gene, (vi) in the guaBA locus, and the clpX gene, (vii) in the guaB gene and the clpPX locus, (viii) in the guaA gene and the clpPX locus, or (ix) in both the guaBA locus and the clpPX locus In one embodiment, attenuated *S. Enteritidis* or *S. Typhimurium* strains are prepared having chromosomal deletions in both the guaBA locus (encoding enzymes involved in guanine nucleotide biosynthesis) and the clpPX locus (encoding an important metabolic ATPase) genes. The mutations of the loci and genes described herein may be any mutation, such as one or more nucleic acid deletions, insertions or substitutions. The mutations may be any deletion, insertion or substitution of the loci or genes that results in a reduction or absence of expression from the loci or genes, or a reduction or absence of activity of a polypeptide encoded by the loci or genes. The mutations may be in the coding or non-coding regions of the loci or genes.

In some embodiments, the chromosomal genome of the *S. Enteritidis* or *S. Typhimurium* strain is modified by removing or otherwise modifying the guaBA locus, and thus blocking the de novo biosynthesis of guanine nucleotides. In some embodiments, a mutation in the guaBA locus inactivates the purine metabolic pathway enzymes IMP dehydrogenase (encoded by guaB) and GMP synthetase (encoded by guaA). In some embodiments, the strains are unable to de novo synthesize GMP, and consequently GDP and GTP nucleotides, which severely limits bacterial growth in mammalian tissues. In some embodiments, the ΔguaBA *S. Enteritidis* or *S. Typhimurium* mutants of the present invention are unable to grow in minimal medium unless supplemented with guanine. In some embodiments, the ΔguaBA *S. Enteritidis* or *S. Typhimurium* mutants of the present invention show a significant reduction in their capability for replication in tissue culture cells after invasion. In some embodiments, ΔguaBA *S. Enteritidis* or *S. Typhimurium* mutants may scavenge guanine nucleotides from the tissues of the mammalian host. However, their assimilation into *S. Enteritidis* or *S. Typhimurium* requires prior dephosphorylation to nucleosides by periplasmic nucleotidases to be incorporated as nucleotide precursors into the guanine salvage pathway. Therefore, as nucleotides are readily available in the intracellular environment of the mammalian host, the attenuation due to the de novo synthesis of guanine nucleotides is due either to the inefficiency of the salvage pathway or to reasons that are obscure to today's knowledge.

The guaA gene of *S. Enteritidis*, which encodes GMP synthetase, is 1578 bp in size (GenBank Accession Number NC_011294 REGION: 2623838-2625415) (SEQ ID NO:1). The guaA gene of *S. Typhimurium*, is 1578 bp in size (GenBank Accession Number NC_003197 REGION: 2622805-2624382) (SEQ ID NO:2). Deletion mutants can be produced by eliminating portions of the coding region of the guaA gene of *S. Enteritidis* or *S. Typhimurium* so that proper folding or activity of GuaA is prevented. For example, about 25 to about 1500 bp, about 75 to about 1400 bp, about 100 to about 1300 bp, or all of the coding region can be deleted. Alternatively, the deletion mutants can be produced by eliminating, for example, a 1 to 100 bp fragment of the guaA gene of *S. Enteritidis* or *S. Typhimurium* so that the proper reading frame of the gene is shifted. In the latter instance, a nonsense polypeptide may be produced or polypeptide synthesis may be aborted due to a frame-shift-induced stop codon. The preferred size of the deletion removes both guaB and guaA, from the ATG start codon of guaB to the stop codon of guaA. Deletions can also be made that extend beyond the guaA gene.

The guaB gene of *S. Enteritidis* which encodes IMP dehydrogenase, is 1467 bp in size (GenBank Accession Number NC_011294 REGION: 2625485-2626951) by in size (SEQ ID NO:3). The guaB gene of *S. Typhimurium* is 1467 bp in size (GenBank Accession Number NC_003197 REGION: 2624452-2625918) (SEQ ID NO:4). Deletion mutants can be produced by eliminating portions of the coding region of the guaB gene of *S. Enteritidis* or *S. Typhimurium* so that proper folding or activity of GuaB is prevented. For example, about 25 to about 1400 bp, about 75 to about 1300 bp, about 100 to about 1200 bp, or all of the coding region can be deleted. Alternatively, the deletion mutants can be produced by eliminating, for example, a 1 to 100 bp fragment of the guaB gene of *S. Enteritidis* or *S. Typhimurium* so that the proper reading frame of the gene is shifted. In the latter instance, a nonsense polypeptide may be produced or polypeptide synthesis may be aborted due to a frame-shift-induced stop codon. The preferred size of the deletion removes both guaB and guaA, from the ATG start codon of guaB to the stop codon of guaA. In some embodiments, deletions can also be made that extend beyond the guaB gene.

The clpP gene of *S. Enteritidis*, which encodes a serine-protease, is 624 bp in size (GenBank Accession Number NC_011294 REGION: 482580-483203) (SEQ ID NO:5). The clpP gene of *S. Typhimurium* is 624 bp in size (GenBank Accession Number NC_003197 REGION: 503210-503833) (SEQ ID NO:6). Deletion mutants can be produced by eliminating portions of the coding region of the clpP gene of *S. Enteritidis* or *S. Typhimurium* so that proper folding or activity of ClpP is prevented. For example, about 25 to about 600 bp, about 75 to about 500 bp, about 100 to about 400 bp, or all of the coding region can be deleted. Alternatively, the deletion mutants can be produced by eliminating, for example, a 1 to 100 bp fragment of the clpP gene of *S. Enteritidis* or *S. Typhimurium* so that the proper reading frame of the gene is shifted. In the latter instance, a nonsense polypeptide may be produced or polypeptide synthesis may be aborted due to a frame-shift-induced stop codon. The preferred size of the deletion is about 25 to 600 bp. Deletions can also be made that extend beyond the clpP gene.

The clpX gene of *S. Enteritidis*, which encodes a chaperone ATPase, is 1272 bp in size (GenBank Accession Number NC_011294 REGION: 483455-484726) (SEQ ID NO:7). The clpX gene of *S. Typhimurium* is 1272 bp in size (GenBank Accession Number NC_003197 REGION: 504085-505356) (SEQ ID NO:8). Deletion mutants can be produced by eliminating portions of the coding region of the clpX gene of *S. Enteritidis* or *S. Typhimurium* so that proper folding or activity of ClpX is prevented. For example, about 25 to about 1200 bp, about 75 to about 1100 bp, about 100 to about 1000 bp, or all of the coding region can be deleted. Alternatively, the deletion mutants can be produced by eliminating, for example, a 1 to 100 bp fragment of the clpX gene of *S. Enteritidis* or *S. Typhimurium* so that the proper reading frame of the gene is shifted. In the latter instance, a nonsense polypeptide may be produced or polypeptide synthesis may be aborted due to a frame-shift-induced stop codon. The preferred size of the deletion is about 75 to 750 bp. Deletions can also be made that extend beyond the clpX gene.

In some embodiments, deletions can be made in any of the loci or genes included herein by using convenient restriction sites located within the loci or genes, or by site-directed mutagenesis with oligonucleotides (Sambrook et al., *Molecular Cloning, A Laboratory Manual*, Eds., Cold Spring Harbor Publications (1989)).

In some embodiments, inactivation of the loci or genes can also be carried out by an insertion of foreign DNA using any convenient restriction site, or by site-directed mutagenesis with oligonucleotides (Sambrook et al., supra) so as to interrupt the correct transcription of the loci or genes. The typical size of an insertion that can inactivate the loci or genes is from 1 base pair to 100 kbp, although insertions smaller than 100 kbp are preferable. The insertion can be made anywhere inside the loci or gene coding regions or between the coding regions and the promoters.

Other methods for the inactivation of the loci and genes include the transfer into *Salmonella* of deletions or insertions made in other enterobacteriaceae guaBA locus, guaA, guaB, clpP or clpX genes, or clpPX locus, transposon-generated deletions, and imprecise excision of DNA insertions.

In some_embodiments, the bacterial loci and genes are mutated using Lambda Red-mediated mutagenesis (Datsenko and Wanner, *PNAS USA* 97:6640-6645 (2000)). Briefly, in step 1 host bacteria targeted for mutation are transformed with a temperature sensitive plasmid encoding lambda Red recombinase. These bacteria are grown in the presence of arabinose to induce lambda Red production. Chromosomal mutagenesis of a target sequence is accomplished by electroporation of the host with linear DNA in which the target gene is replaced with an antibiotic resistance marker. This DNA also encodes short regions of flanking chromosomal sequences to allow for chromosomal integration of the resistance marker by lambda Red-mediated homologous recombination. Recombinants are selected for on solid media containing the appropriate antibiotic, and incubated at a temperature facilitating the loss of the plasmid encoding lambda Red recombinase. For step 2, removal of the chromosomal resistance marker is facilitated by transforming the bacteria with a temperature sensitive plasmid encoding FLP recombinase, which targets unique FRT recombination sites engineered to flank the antibiotic resistance marker now present in the host chromosome. Transformants are grown at temperatures permissive for the presence of the FLP recombinase which is expressed constitutively. In some embodiments, mutants are screened via PCR, grown at a temperature to facilitate loss of the plasmid encoding FLP recombinase, and selected for storage.

In some embodiments, the attenuated *S. Enteritidis* or *S. Typhimurium* strains of the present invention may contain mutations in one or more additional genes. While an extensive discussion of additional attenuating mutations of *Salmonella* spp. is provided in U.S. Pat. No. 6,682,729, exemplary genes include those encoding various biochemical pathways, global regulatory systems, heat shock proteins, other regulatory genes, and putative virulence properties. Specific examples of such attenuating mutations include, but are not limited to: (i) auxotrophic mutations, such as aro, nad, thy, and asd mutations; (ii) mutations that inactivate global regulatory functions, such as cya, crp, phoP/phoQ, $phoP^c$ and ompR mutations; (iii) mutations that modify the stress response, such as recA, htrA, htpR, hsp and groEL mutations; (iv) mutations in specific virulence factors, such as pag and prg (v) mutations that affect DNA topology, such as topA mutations; (vi) mutations that modify suicide systems, such as sacB, nuc, hok, gef, kil, and phlA mutations; (vii) mutations that introduce suicide systems, such as lysogens encoded by P22, λ murein transglycosylase and S-gene; and (viii) mutations that disrupt or modify the correct cell cycle, such as minB mutations. Such mutations are permissible, provided however, that such mutations do not inactivate loci involved in generation of surface polysaccharides which would alter the surface OPS immunogens.

Formulations, Dosages and Modes of Administering the Attenuated Strains

The attenuated strains of the present invention may be administered to a subject to induce an immune response. In one embodiment, the strains of the present invention are administered in a pharmaceutical formulation.

The pharmaceutical formulations of the strains of the present invention may include pharmaceutically acceptable carriers, excipients, other ingredients, such as adjuvants. Pharmaceutically acceptable carriers, excipients, other ingredients are those compounds, solutions, substances or materials that are compatible with the strains of the present invention and are not unduly deleterious to the recipient thereof, or diminish intended immune responses. In particular, carriers, excipients, other ingredients of the present invention are those useful in preparing a pharmaceutical formulation that is generally safe, non-toxic and neither biologically nor otherwise undesirable, and that may present pharmacologically favorable profiles, and includes carriers, excipients, other ingredients that are acceptable for veterinary use as well as human pharmaceutical use.

Suitable pharmaceutically acceptable carriers and excipients are well known in art and can be determined by those of skill in the art as the clinical situation warrants. The skilled artisan will understand that diluents are included within the scope of the terms carriers and excipients. Examples of suitable carriers and excipients include saline, buffered saline, dextrose, water, glycerol, ethanol, more particularly: (1) Dulbecco's phosphate buffered saline, pH about 7.4, containing about 1 mg/ml to 25 mg/ml human serum albumin, (2) 0.9% saline (0.9% w/v NaCl), (3) 5% (w/v) dextrose, and (4) water.

The mode of administration of the immunizing compositions of the present invention may be any suitable delivery means and/or methods that results in the induction of an immune response in the subject. Delivery means may include, non-parenteral, e.g., oral, nasal, intravaginal, pulmonary (inhalation), ophthalmic, rectal administration, or by any other mode that results in the immunogenic composition contacting mucosal tissues. In one embodiment, one or more attenuated strains are administered orally.

In one embodiment of the present invention, the immunizing compositions exist as an atomized dispersion for delivery by inhalation. Various liquid and powder formulations can be prepared by conventional methods for inhalation into the lungs of the subject to be treated. The atomized dispersion of the immunizing compositions typically contains carriers common for atomized or aerosolized dispersions, such as buffered saline and/or other compounds well known to those of skill in the art. The delivery of the immunogenic compositions via inhalation has the effect of rapidly dispersing the immunizing compositions to a large area of mucosal tissues.

Additionally, immunizing compositions also exist in a liquid form. The liquid can be for oral dosage, for ophthalmic or nasal dosage as drops, or for use as an enema or douche. When the immunizing composition is formulated as a liquid, the liquid can be either a solution or a suspension of the immunizing composition. There are a variety of suitable formulations for the solution or suspension of the immunizing composition that are well know to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the immunizing compositions, wetting agents, sweeteners, and coloring and flavoring agents.

Delivery of the described immunizing compositions in liquid form via oral, rectal, and vaginal dosage exposes the mucosa of the gastrointestinal and urogenital tracts to the immunizing compositions. A suitable dose, stabilized to resist the pH extremes of the stomach, delivers the immunizing composition to all parts of the gastrointestinal tract, especially the upper portions thereof. Any methods of stabilizing the immunizing composition in a liquid oral dosage such that the effective delivery of the composition is distributed along the gastrointestinal tract are contemplated for use with the immunizing compositions described herein, including capsules and a resuspended buffer solution to protect the attenuated bacteria against the acidic pH. The particular pharmaceutically acceptable carriers or diluents employed are not critical to the present invention, and are conventional in the art. Examples of diluents include: buffers for buffering against gastric acid in the stomach, such as citrate buffer (pH 7.0) containing sucrose, bicarbonate buffer (pH 7.0) alone or bicarbonate buffer (pH 7.0) containing ascorbic acid, lactose, and optionally aspartame (Levine et al, Lancet, II:467-470 (1988)). Examples of carriers include: proteins, e.g., as found in skim milk; sugars, e.g., sucrose; or polyvinylpyrrolidone.

Delivery of the described immunizing strains in liquid form via ophthalmic drops exposes the mucosa of the eyes and associated tissues to the immunizing compositions. A typical liquid carrier for eye drops is buffered and contains other compounds well known and easily identifiable to those of skill in the art.

Delivery of the described immunizing compositions in liquid form via nasal drops or aerosol exposes the mucosa of the nose and sinuses and associated tissues to the immunizing compositions. Liquid carriers for nasal drops are typically various forms of buffered saline.

The attenuated *S. Typhimurium* and *S. Enteritidis* strains of the present invention may be administered to a subject in conjunction with other suitable pharmacologically or physiologically active agents, e.g., antigenic and/or other biologically active substances.

The amount and rate of administration of the immunizing compositions of the present invention may be readily determined by those of ordinary skill in the art without undue experimentation, such as by use of conventional antibody titer determination techniques and conventional bioefficacy/biocompatibility protocols employed after vaccination. The amount and rate of administration will vary based on factors such as the weight and health of the subject, the identity of the bacteria being administered to the subject, the identity of the polypeptide being expressed in those strains engineered to express a selected antigen, the desired therapeutic effect, the desired time span of bioactivity, and the mode of administration of the immunizing composition.

In general, the amount of an immunizing composition administered to a subject is an amount sufficient to induce an immune response in the subject to a *S. Typhimurium* or *S. Enteritidis* strain or to the selected antigen being expressed by the *S. Typhimurium* or *S. Enteritidis* strain (an immunologically-effective amount). In a preferred embodiment, the immune response is a protective immune response.

In some embodiments, the dosage employed for mucosal delivery will contain about $10^5$ cfu to $10^{10}$ cfu of the *S. Typhimurium* or *S. Enteritidis* strain, preferably about $10^5$ cfu to $10^7$ cfu, or about $10^6$ cfu to $10^9$ cfu. Formulations for oral administration comprise about $10^6$ cfu to $10^{10}$ cfu of the *S. Typhimurium* or *S. Enteritidis* strain, preferably about $10^8$ cfu to $10^9$ cfu, and the formulation is in a capsule or resuspended in a buffer solution to protect the attenuated bacteria against the acidic pH in the stomach. Formulations for nasal administration comprise about $10^5$ cfu to $10^{10}$ cfu of the *S. Typhimurium* or *S. Enteritidis* strain, preferably about $10^7$ cfu to $10^8$ cfu, and is used for intranasal administration in which the bacteria is given in drops or in aerosol.

The immunizing compositions of *S. Typhimurium* or *S. Enteritidis* strains of the invention may be administered in a single dose, or in multiple doses over prolonged periods of time. In particular, the immunizing compositions may be administered over a period of one week, two weeks, three weeks, one month, six weeks, two months, ten weeks, three months, four months, six months, one year, or for extended periods longer than one year.

The immunizing compositions of *S. Typhimurium* or *S. Enteritidis* may be provided in dosage units for uniform dosage and ease of administration. Each dosage unit form contains a predetermined quantity of the strains of the present invention calculated to produce a desired immune response, in association with a pharmaceutically acceptable carrier, excipient, or other ingredient.

In some embodiments, the compositions of *S. Typhimurium* or *S. Enteritidis* are administered as live vaccines. In other embodiments, the *S. Typhimurium* or *S. Enteritidis* are killed formulations, e.g., by heat, prior to administration.

Methods of Inducing an Immune Response

The present invention also includes methods of inducing an immune response in a subject. The immune response may be to the attenuated *S. Typhimurium* or *S. Enteritidis* strains, a conjugate vaccine of the invention, or both.

Vaccine strategies are well known in the art and therefore the vaccination strategy encompassed by the invention does not limit the invention in any manner. In certain aspects of the invention, the conjugate vaccine is administered alone in a single dose or administered in sequential doses. In other aspects of the invention, the conjugate vaccine is administered as a component of a homologous or heterologous prime/boost regimen. In some embodiments of the invention, a single boost is used. In some embodiments of the invention, multiple boost immunizations are performed. In particular aspects of the invention drawn to heterologous prime/boost, a mucosal bacterial prime/parenteral conjugate boost immunization strategy is used. For example, one or more attenuated *S. Typhimurium* or *S. Enteritidis* strains as taught herein is administered orally and subsequently boosted parentally with a conjugate vaccine of homologous OPS from *S. Typhimurium* or *S. Enteritidis* and a homologous flagellin protein from *S. Typhimurium* or *S. Enteritidis* as described herein.

In one embodiment, the method of inducing an immune response comprises administering one or more of the *S. Typhimurium* or *S. Enteritidis* strains of the present invention to a subject in an amount sufficient to induce an immune response in the subject.

In a further embodiment, the method of inducing an immune response comprises administering a pharmaceutical formulation comprising one or more of the strains of the present invention to a subject in an amount sufficient to induce an immune response in the subject (an immunologically-effective amount).

In a further embodiment, the method of inducing an immune response comprises administering a conjugate vaccine of the present invention to a subject in an amount sufficient to induce an immune response in the subject (an immunologically-effective amount).

As used herein, an "immune response" is the physiological response of the subject's immune system to an immunizing composition. An immune response may include an innate immune response, an adaptive immune response, or both. In some embodiments of the present invention, the immune response is a protective immune response. A protective immune response confers immunological cellular memory upon the subject, with the effect that a secondary exposure to the same or a similar antigen is characterized by one or more of the following characteristics: shorter lag phase than the lag phase resulting from exposure to the selected antigen in the absence of prior exposure to the immunizing composition; production of antibody which continues for a longer period than production of antibody resulting from exposure to the selected antigen in the absence of prior exposure to the immunizing composition; a change in the type and quality of antibody produced in comparison to the type and quality of antibody produced upon exposure to the selected antigen in the absence of prior exposure to the immunizing composition; a shift in class response, with IgG antibodies appearing in higher concentrations and with greater persistence than IgM, than occurs in response to exposure to the selected antigen in the absence of prior exposure to the immunizing composition; an increased average affinity (binding constant) of the antibodies for the antigen in comparison with the average affinity of antibodies for the antigen resulting from exposure to the selected antigen in the absence of prior exposure to the immunizing composition; and/or other characteristics known in the art to characterize a secondary immune response.

In some embodiments, the invention is directed to methods of inducing an immune response, comprising administering to a subject in need thereof an effective amount of a conjugate vaccine comprising an O polysaccharide (OPS) and a flagellin protein or a fragment or a derivative thereof, wherein the OPS and flagellin protein of the conjugate vaccine are characteristic of group B or group D *Salmonella* serovars, such as *S. Typhimurium*, or *S. Enteritidis*, respectively.

In some embodiments, the invention is directed to methods of inducing an immune response, comprising administering to a subject in need thereof a vaccine comprising an immunologically-effective amount of genetically modified attenuated *Salmonella* serovar as described herein selected from the group consisting of *S. Typhimurium* and *S. Enteritidis*.

In another aspect, the invention is directed to methods of inducing an immune response, comprising administering to a subject in need thereof a first vaccine comprising an immunologically-effective amount of genetically modified attenuated *Salmonella* serovar as described herein and a second vaccine comprising an immunologically-effective amount of a conjugate comprising the homologous OPS and flagellin protein or a fragment or a derivative thereof. In one embodiment, a subject is orally administered an attenuated live strain of *S. Typhimurium* and/or *S. Enteritidis* of the invention, followed by a booster immunization administered parenterally, comprising a conjugate vaccine of the invention, wherein the conjugate vaccine is a *Salmonella* Group B and/or D OPS covalently linked to a flagellin protein. The present invention is not limited to the order in which bacteria and conjugate vaccines are administered. In some embodiments, the time interval between the first and second vaccinations is one week, two weeks, three weeks, 1 month, 2 months, 3 months, 4 months, 5 months, 6 months, 7 months, 8 months, 9 months, 10 months, 11 months, one year, 1.5 years and two years. Immunization schedules have been scheduled and administered at 1 month intervals, with a priming immunization followed by two sequential booster immunizations.

In some embodiments, the vaccines of the invention are administered with a pharmaceutically acceptable carrier, such that it provides host immunity against an infection.

The term "carrier" denotes an organic or inorganic ingredient, natural or synthetic, with which the active ingredient is combined to facilitate the application without diminishing the immunogenicity of the vaccine. The characteristics of the carrier depend on the nature of the vaccine and the route of administration. Physiologically and pharmaceutically-acceptable carriers include diluents, fillers, salts, buffers, stabilizers, solubilizers, and other materials which are well known in the art. The term "pharmaceutically acceptable" is used to refer to a non-toxic material that is compatible with a biological system such as a cell, cell culture, tissue, or organism.

In practicing immunization protocols for treatment and/or prevention, an immunologically-effective amount of conjugate is administered to a subject. As used herein, the term "immunologically-effective amount" means the total amount of therapeutic agent (e.g., conjugate) or other active component that is sufficient to show an enhanced immune response in the subject. When "immunologically-effective amount" is applied to an individual therapeutic agent administered alone, the term refers to that therapeutic agent alone. When applied to a combination, the term refers to combined amounts of the ingredients that result in the therapeutic effect, whether administered in combination, serially or simultaneously, and regardless of order of administration.

The particular dosage depends upon the age, weight, sex and medical condition of the subject to be treated, as well as on the method of administration. Suitable doses can be readily determined by those of skill in the art.

The conjugate vaccines of the invention can be administered by either single or multiple dosages of an effective amount. In some embodiments, an effective amount of the compositions of the invention can vary from 0.01-5,000 μg/ml per dose. In other embodiments, an effective amount of the composition of the invention can vary from 0.1-500 μg/ml per dose, and in other embodiments, it can vary from 10-300 μg/ml per dose. In one embodiment, the dosage of the conjugate administered will range from about 10 μg to about 1000 μg. In another embodiment, the amount administered will be between about 20 μg and about 500 μg. In some embodiments, the amount administered will be between about 75 μg and 250 μg. Greater doses may be administered on the basis of body weight. The exact dosage can be determined by routine dose/response protocols known to one of ordinary skill in the art.

In some embodiments, the amount of conjugate that provides an immunologically-effective amount for vaccination against bacterial infection is from about 1 μg or less to about 100 μg or more. In some embodiments, it is from about 2, 3, 4, 5, 6, 7, 8, 9, 10, 15, 20, 25, 30, 35, 40, 45 or 50 μg to about 55, 60, 65, 70, 75, 80, 85, 90, or 95 μg per kg body weight. In a preferred embodiment, the immunologically-effective amount for vaccination against bacterial infection is from 0.01 μg to 10 μg.

The term "subject" as used herein, refers to animals, such as mammals. For example, mammals contemplated include humans, primates, dogs, cats, sheep, cattle, goats, pigs, horses, chickens, mice, rats, rabbits, guinea pigs, and the like. The terms "subject", "patient", and "host" are used interchangeably.

The conjugate vaccine of the present invention may confer resistance to *S. Enteritidis* or *S. Typhimurium* by either passive immunization or active immunization. In one embodiment of passive immunization, the vaccine is provided to a subject (i.e. a human or mammal), and the elicited antisera is recovered and directly provided to a recipient suspected of having an infection caused by *S. Enteritidis* or *S. Typhimurium.*

The ability to label antibodies, or fragments of antibodies, with toxin labels provides an additional method for treating *S. Enteritidis* or *S. Typhimurium* infections when this type of passive immunization is conducted. In this embodiment, antibodies, or fragments of antibodies which are capable of recognizing the *S. Enteritidis* or *S. Typhimurium* antigens are labeled with toxin molecules prior to their administration to the patient. When such a toxin derivatized molecule binds to a *S. Enteritidis* or *S. Typhimurium* cell, the toxin moiety will cause the death of the cell.

In some embodiments, the present invention provides a means for preventing or attenuating infection by *S. Enteritidis* or *S. Typhimurium*, or by organisms which have antigens that can be recognized and bound by antisera to the polysaccharide and/or protein of either the conjugated vaccine or the attenuated bacterial vaccine strains. As used herein, a vaccine is said to prevent or attenuate a disease if its administration to an individual results either in the total or partial attenuation (i.e. suppression) of a symptom or condition of the disease, or in the total or partial immunity of the individual to the disease.

The administration of the vaccine (or the antisera which it elicits) may be for either a "prophylactic" or "therapeutic" purpose. When provided prophylactically, the vaccine is provided in advance of any symptom of *S. Enteritidis* or *S. Typhimurium* infection. The prophylactic administration of the vaccine serves to prevent or attenuate any subsequent infection. When provided therapeutically, the vaccine is provided upon the detection of a symptom of actual infection. The therapeutic administration of the vaccine serves to attenuate any actual infection.

Either the conjugate vaccines (or antisera which it elicits) or the attenuated bacterial vaccine strains of the present invention may, thus, be provided either prior to the onset of infection (so as to prevent or attenuate an anticipated infection) or after the initiation of an actual infection.

The invention also provides a method for inducing an immune response which comprises administering to an individual, suspected of being at risk for infection caused by *S. Enteritidis* or *S. Typhimurium*, an immunologically-effective amount of an antisera elicited from the exposure of a second individual to a conjugate or bacterial vaccine (or combinations thereof) of the invention, such that it provides host immunity to the infection.

The conjugate vaccine of the invention may be administered to warm-blooded mammals of any age. The conjugate vaccines can be administered as a single dose or in a series including one or more boosters. In some embodiments, the immunization schedule would involve a primary series of three immunizations with a spacing of 1-2 months between the doses. In some settings a booster dose could be administered ~6-12 months later. For example, an infant can receive three doses at 6, 10 and 14 weeks of age (schedule for infants in sub-Saharan Africa) or at 2, 4, and 6 months of life (schedule for U.S. infants). U.S. infants might receive a booster at 12-18 months of age. Another target population would be U.S. elderly who would likely receive 2-3 doses spaced 1-2 months apart.

In some embodiments, the conjugates can be administered concomitantly with (or in some instances even in combination with) various vaccines either currently being used or in development, whether intended for human or non-human subjects. Examples of vaccines for human subjects and directed to infectious diseases include the combined diphtheria and tetanus toxoids; pertussis whole cell vaccine; acellular pertussis vaccine; inactivated or live intranasal influenza vaccines; 7-valent, 10-valent or 13-valent pneumococcal conjugate vaccines; 23-valent pneumococcal vaccine (relevant to adults, particularly elderly); live measles vaccine; live mumps vaccine; live rubella vaccine; live varicella vaccine; Bacille Calmette-Guerin (BCG) tuberculosis vaccine; hepatitis A vaccine; hepatitis B vaccine; rabies vaccine (e.g., human diploid cell vaccine); inactivated polio vaccine; live oral polio vaccine; bivalent or quadrivalent meningococcal polysaccharide vaccine; monovalent (group A) or quadrivalent meningococcal conjugate vaccine; yellow fever live virus vaccine; oral or parenteral typhoid vaccines; oral cholera vaccines; Japanese B encephalitis killed virus vaccine; rotavirus vaccine; and other commercially available and experimental vaccines.

Methods of Manufacture of a Flagellin Protein Derived from *S. Enteritidis* or *S. Typhimurium*

When generating attenuated vaccines for use as live oral vaccines or for the improved manufacture of components used to make a conjugate vaccine (including, for example, OPS and a flagellin protein), attention to the degree of attenuation must be considered. In regard to large-scale manufacturing, attenuation is particularly important so as to ensure safety in the manufacturing process (including, for example, environmental and occupational health safety). Thus, attenuated *S. Enteritidis* or *S. Typhimurium* strains to be used must be sufficiently and appropriately attenuated to ensure safety for oral administration to humans (and other mammals at risk of NTS disease) but also for large-scale fermentation of *S. Enteritidis* or *S. Typhimurium* to produce components for making conjugate vaccines.

In particular, aspects of the invention are drawn to the large-scale fermentation of *S. Enteritidis* or *S. Typhimurium* strains to derive components for making a conjugate vaccine. In some embodiments, the attenuated strain produces, for example, more flagella than wild-type *S. Enteritidis* or *S. Typhimurium* or exports flagellin protein as monomers rather than as polymerized flagella filaments.

In certain aspects of the invention, an attenuated strain having increased expression of flagella compared to a wild-type strain is particularly advantageous from at least a manufacturing perspective. In particular aspects of the invention, an attenuated *S. Enteritidis* or *S. Typhimurium* strain having one or more mutations described herein leading to attenuation and hyperflagellation can be used either for manufacturing as an oral vaccine or for improved, safer and more economical large-scale production of components to make a conjugate vaccine. For example, an attenuated strain of *S. Enteritidis* or *S. Typhimurium* having a mutation in the guaBA locus, the guaB gene, or the guaA gene, and mutation in the clpP gene (or clpPX locus) produces an attenuated and phenotypically hyperflagellated strain. Methods of purification of a flagellin protein from whole flagella are known in the art or can be readily modified by one of ordinary skill in the art using methods know in the art. For example, by modifying the method of Ibrahim et al., purification of flagella is achieved; below pH 3.0, flagella dissociate into flagellin subunits (Ibrahim et al. *J. Clin. Microbiol.* 1985; 22:1040-4. Further methods for purification include adaptation of the mechanical shearing, and sequential centrifugation steps for purification of flagellin in flagella from bacterial cells. Modern purification methods and clpP mutants should markedly increase yield and purity of a flagellin protein used to construct a conjugate vaccine of the invention (see, for example, Ogushi et al. *J. Biol. Chem.* 2001; 276:30521-6; Yoon et al. *Infect. Immun.* 2008; 76:1282-8).

In other aspects of the invention, export of a flagellin protein monomer from an attenuated *S. Enteritidis* or *S. Typhimurium* strain is used to derive a flagellin protein used to construct a conjugate vaccine of the invention. For example, a mutation in the fliD gene, flgL gene, or flgK gene causes export of flagellin monomers into the supernatant. Therefore, in some embodiments, an attenuated *S. Enteritidis* or *S. Typhimurium* strain of the invention having a primary attenuating mutation in either the guaBA locus, the guaB gene, or the guaA gene, may be further engineered to contain an additional mutation in either the fliD gene, flgL gene, or flgK gene to export FliC monomers into the extracellular medium. In some embodiments, such attenuated *S. Enteritidis* or *S. Typhimurium* strain having a primary attenuating mutation further has a mutation in the clpP gene (or clpPX locus). Such strains will serve as a single source for both safe production of a conjugate vaccine as well as for use as a live vaccine strain.

In a particular embodiment of the invention, *S. Enteritidis* or *S. Typhimurium* containing a guaBA mutation and a fliD mutation is made and used to derive a flagellin protein in monomeric subunit form to be used to construct a homologous conjugate vaccine of the invention. Mutation of both the guaBA and fliD gene can be accomplished by a number of methods, including the method of lambda Red-mediated mutagenesis mentioned in previous sections of the invention.

In addition to the attenuated *S. Enteritidis* or *S. Typhimurium* strains described herein for vaccination purposes, and for deriving a flagellin protein used as a component of the conjugate vaccine described herein, these strains can be used to derive OPS that are used as a component of the conjugate vaccine described herein. The invention also encompasses any of the foregoing mutations in any combination that provides for maximum efficacy or manufacturing results (e.g., any combination of mutations in guaBA locus, the clpPX locus, the guaB gene, guaA gene, clpP gene, clpX gene, fliD gene, flgL gene, flgK gene, or any other mutation described herein which can be made in all possible combinations or variations).

Kits

In some embodiments, the invention is directed to kits comprising vaccines of the invention. Such kits can be provided to an administering physician or other health care professional. In some embodiments, the kit is a package which houses a container which contains the conjugate vaccine composition and instructions for administering the conjugate vaccine composition to a subject. In some embodiments, the kit can also contain one or more other therapeutic agents. The kit can optionally contain one or more diagnostic tools and instructions for use. For example, a vaccine cocktail containing two or more vaccines can be included, or separate pharmaceutical compositions containing different vaccines or therapeutic agents. The kit can also contain separate doses of the conjugate vaccine for serial or sequential administration. The kit can also contain a composition comprising one or more attenuated *Salmonella* strains of the invention. The kit can contain suitable delivery devices, e.g., syringes, inhalation devices, and the like, along with instructions for administrating the therapeutic agents. The kit can optionally contain instructions for storage, reconstitution (if applicable), and administration of any or all therapeutic agents included. The kits can include a plurality of containers reflecting the number of administrations to be given to a subject. If the kit contains a first and second container, then a plurality of these can be present.

While the invention has been described with reference to certain particular examples and embodiments herein, those skilled in the art will appreciate that various examples and embodiments can be combined for the purpose of complying with all relevant patent laws (e.g., methods described in specific examples can be used to describe particular aspects of the invention and its operation even though such are not explicitly set forth in reference thereto).

Example 1

Construction of Safe *S. Enteritidis* and *S. Typhimurium* Strains

A key aspect of the invention is the construction of clinically well tolerated attenuated strains of *S. Enteritidis* and *S. Typhimurium* for use as live oral vaccines; for safer, more economical manufacture of purified OPS and flagellin subunit protein to prepare conjugate vaccine for parenteral administration, as well as using these strains in a heterologous mucosal prime/parenteral boost immunization strategy to broaden both the immunogenicity and protective capacity of the conjugate vaccines. We therefore deleted both the guaBA and clpP genes from both *S. Enteritidis* strain R11 and *S. Typhimurium* strain I77, using a highly efficient site-directed lambda Red-mediated mutagenesis technique. Deletion regions in the chromosomes of each of the resulting attenuated strains were sequenced to confirm that only the intended genes and DNA sequences had been removed. Having created these basic attenuated candidate vaccine strains, we then sequentially introduced further mutations into fliD to secrete FliC monomers, as well as deleting the fljBA locus encoding phase 2 flagellin FlgB and the FliC repressor protein FljA from *S. Typhimurium* (*S. Enteritidis* encodes only phase 1 flagella). A list of the attenuated strains now available for purification of OPS and FliC conjugate components is shown in Table 1.

TABLE 1

Attenuated NTS strains and expected levels of flagellin production*

| Strain | Chromosomal deletions | Expected phenotype |
|---|---|---|
| *S. Typhimurium* | | |
| CVD 1920 | guaBA | Wildtype FliC and FljB flagella |
| CVD 1921 | guaBA clpP | Hyper-expression of FliC and FljB flagella |
| CVD 1922 | guaBA fliD | Expression of FliC and FljB monomers |
| CVD 1923 | guaBA clpP fliD | Hyper-expression of FliC and FljB monomers |
| CVD 1924 | guaBA clpP fljBA | Hyper-expression of FliC flagella |
| CVD 1925 | guaBA clpP fliD fljBA | Hyper-expression of FliC monomers |
| *S. Enteritidis* | | |
| CVD 1940 | guaBA | Wildtype FliC expression |
| CVD 1941 | guaBA clpP | Hyper-expression of FliC flagella |
| CVD 1942 | guaBA fliD | Expression of FliC monomers |
| CVD 1943 | guaBA clpP fliD | Hyper-expression of FliC monomers |

*All strains containing the guaBA deletion are dependent on guanine supplementation for growth A detailed discussion of the engineering of attenuated *S. Typhimurium* strain CVD 1925 is included here. Since the homologous chromosomal regions for both *S. Typhimurium* and *S. Enteritidis* are nearly identical for guaBA, clpPX, and fliD, primers used for lambda Red-mediated mutagenesis were identical, so mutagenesis of *S. Typhimurium* illustrates the engineering steps taken for generation of mutants for both serovars (with the exception of fljBA which is not encoded by *S. Enteritidis*). All primers used for this work are listed in Table 2).

TABLE 2

| Name | Sequence | SEQ ID NO: |
|---|---|---|
| P1 | GTGTAGGCTGGAGCTGCTTC | 9 |
| P4 | ATTCCGGGGATCCGTCGACC | 10 |

TABLE 2-continued

| Name | Sequence | SEQ ID NO: |
|---|---|---|
| guaBAF | TGTTTATGCTGCTGATCGAAC | 11 |
| guamutR2 | **GAAGCAGCTCCAGCCTACAC**GGG CAATATCTCACCTGG | 12 |
| guamutF3 | **GGTCGACGGATCCCCGGAT**GCCG ATAATCCTTCCTGTG | 13 |
| guaBAR2 | ATAACCTGGACACTTCTGAG | 14 |
| guaBAF2 | TTCGAAGTGATCACCCCAAC | 15 |
| guaBAR3 | TATTTGGGCTGAATCGCCAC | 16 |
| clpPXF | TAAGCGTCGTGTAGTTGTCG | 17 |
| clpmutR | **GAAGCAGCTCCAGCCTACA**CATT ACATTTCCGTCTCCTGG | 18 |
| clpmutF3 | **GGTCGACGGATCCCCGGAAT**TGA TGCCCTGGACGCAAGTG | 19 |
| clpPR | TAACGTAATCGTCCAGGTGG | 20 |
| clpPXF2 | AGAAACAGGCTCTGGAGCTG | 21 |

TABLE 2-continued

| Name | Sequence | SEQ ID NO: |
|---|---|---|
| CVOL88 | ACGGCGTGTTTACAGGAAAAACGA AAGGGG | 22 |
| fljBAF2 | TATGACACTTGATCATGTGATG | 23 |
| fljBAmutR3 | **GAAGCAGCTCCAGCCTACA**CCCA ATAAATCGTGTGGCTG | 24 |
| fljBAmutF3 | **GGTCGACGGATCCCCGGAAT**CGC CTACGGTAATAAAAAATTC | 25 |
| fljBAR | TGAGAACTTCAGCAAATCGAC | 26 |
| fljBAF3 | ACGTCATAAATCGAACAAGTCG | 27 |
| fljBAR2 | AGCTTCAGCATTGCATCAGC | 28 |

TABLE 2-continued

| Name | Sequence | SEQ ID NO: |
|---|---|---|
| t5FliD | GAATTCtcacgcacacgctgcagg | 29 |
| 5FliD-rev | GCTAGCacctaatgatgaaattgaagccatgc | 30 |
| 5FRT-aph | GAATTCGCTAGCGCTGGAGCTGCTT Cgaagttc | 31 |
| 3FRT-aph | ctcgagTTCCGGGGATCCGTCGACCTG CAGTTC | 32 |
| 3fliD | GGATCCgctatgaacaagtcctgataacagaggt | 33 |
| 3FliD-rev | CTCGAGttaacgagactcctggaaagatgctttc ggtgaaatctgc | 34 |
| g1020 | GATTGACTGAGCAGCGCAATACGC TG | 35 |
| g1028 | GGTGATTTCAGCCTGGATGGAGTCG A | 36 |

* Bold indicates DNA complementary to primers P1 and P4

Figure 2:
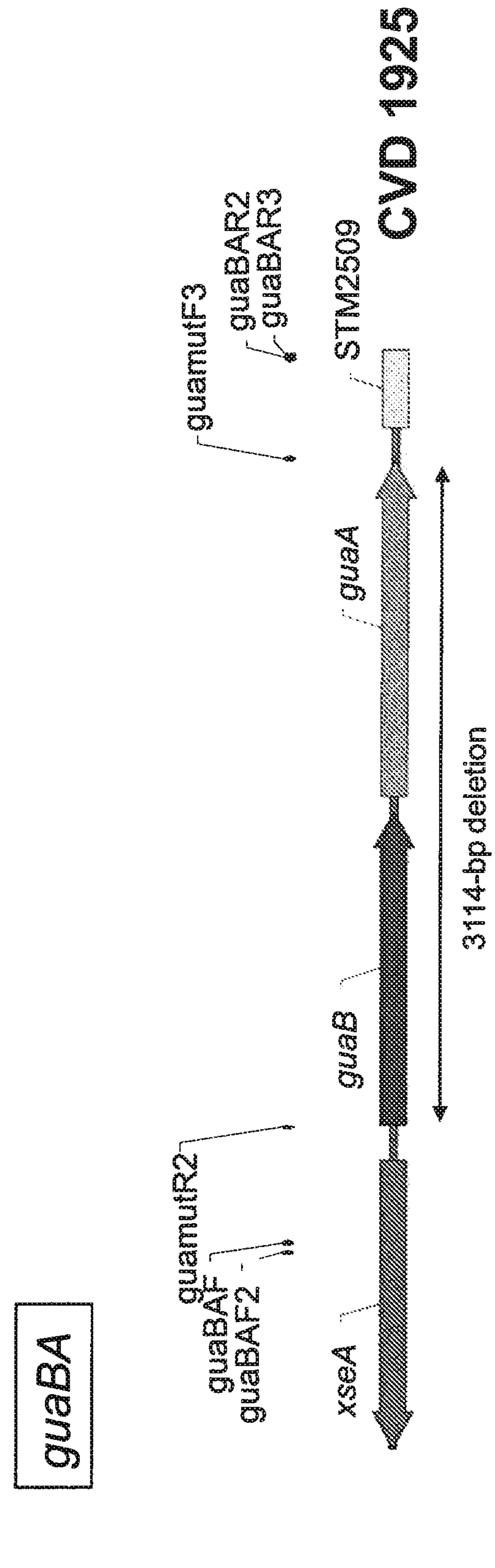
FIG. 2. Deletion of chromosomal guaBA from attenuated *Salmonella enterica* serovar *Typhimurium* vaccine strain CVD 1925 using lambda Red-mediated mutagenesis.

The guaBA locus was deleted from *S. Typhimurium* and *S. Enteritidis* using the lambda Red recombinase system. DNA upstream of guaB was amplified using primers guaBAF (SEQ ID NO: 11) and guamutR2 (SEQ ID NO:12) and DNA downstream of guaA was amplified using primers guamutF3 (SEQ ID NO:13) and guaBAR2 (SEQ ID NO:14) (FIG. 2). The kanamycin resistance cassette from pKD13 was amplified using primers P1 (SEQ ID NO:9) and P4 (SEQ ID NO:10). The 3 PCR products were combined and overlapping PCR was used to generate guaBA::$Km^R$ DNA. The $Km^R$ cassette was integrated into the genome by homologous recombination using lambda Red recombinase and then removed using Flp encoded by pCP20 resulting in replacement of guaBA with an ~80-bp scar sequence. The deletion was verified by amplification using primers guaBAF2 (SEQ ID NO:15) and guaBAR3 (SEQ ID NO:16) that are outside the deleted region and the PCR product from CVD 1925 was sequenced (SEQ ID NO:37).

Figure 3:
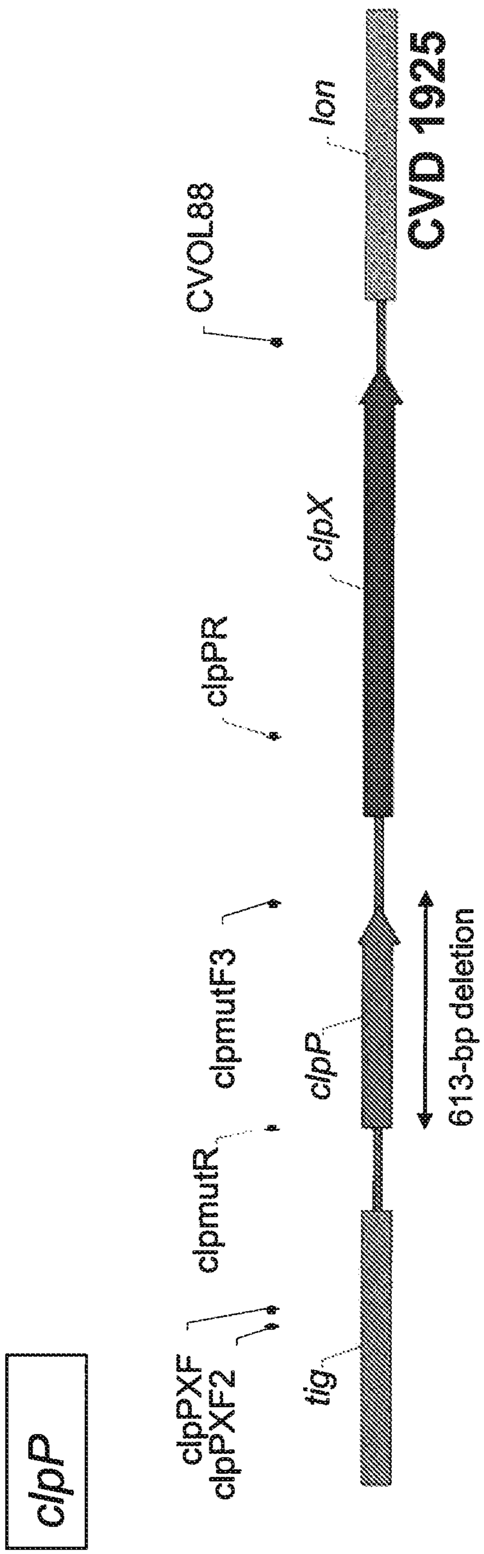
FIG. 3. Deletion of chromosomal clpP from attenuated *Salmonella enterica* serovar *Typhimurium* vaccine strain CVD 1925 using lambda Red-mediated mutagenesis.

For deletion of the clpP gene, DNA upstream of clpP was amplified using primers clpPXF (SEQ ID NO:17) and clpmutR (SEQ ID NO:18) and DNA downstream of clpP was amplified using primers clpmutF3 (SEQ ID NO:19) and clpPR (SEQ ID NO:20) (FIG. 3). The kanamycin resistance cassette from pKD13 was amplified using primers P1 (SEQ ID NO:9) and P4 (SEQ ID NO:10). The 3 PCR products were combined and overlapping PCR was used to generate clpP::$Km^R$ DNA. The $Km^R$ cassette was integrated into the genome by homologous recombination using lambda Red recombinase and then removed using Flp encoded by pCP20 resulting in replacement of clpP with an ~80-bp scar sequence. The resulting mutant has a clpP polar mutation (prevents translation of clpX, the second gene in the operon). The deletion was verified by amplification using primers clpPXF2 (SEQ ID NO:21) and CVOL88 (SEQ ID NO:22) that are outside the deleted region and the PCR product from CVD 1925 was sequenced (SEQ ID NO:38).

Figure 4:
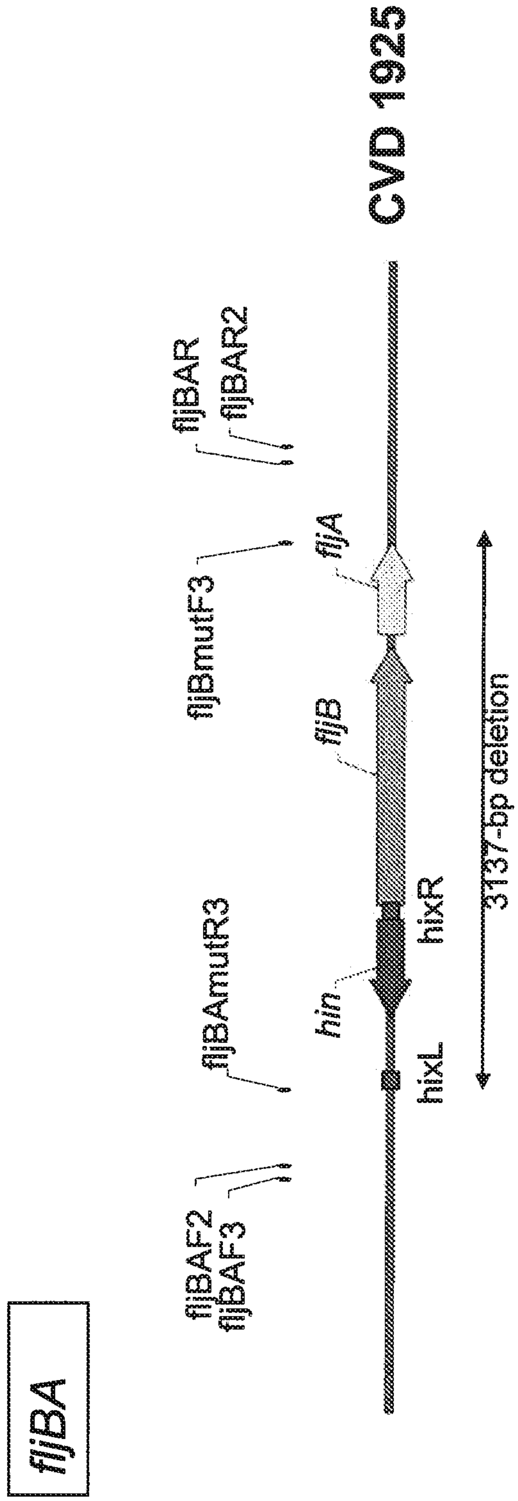
FIG. 4. Deletion of the chromosomal fljBA locus from attenuated *Salmonella enterica* serovar *Typhimurium* vaccine strain CVD 1925 using lambda Red-mediated mutagenesis.

The fljBA locus was deleted from *S. Typhimurium* by amplifying DNA upstream of hixL (the upstream site recognized by the recombinase encoded by hin) using primers fljBAF2 (SEQ ID NO:23) and fljBAmutR3 (SEQ ID NO:24) and DNA downstream of fljA was amplified using primers fljBAmutF3 (SEQ ID NO:25) and fljBAR (SEQ ID NO:26) (FIG. 4). The kanamycin resistance cassette from pKD13 was amplified using primers P1 (SEQ ID NO:9) and P4 (SEQ ID NO:10). The 3 PCR products were combined and overlapping PCR was used to generate fljBA::$Km^R$ DNA. The $Km^R$ cassette was integrated into the genome by homologous recombination using lambda Red recombinase and then removed using Flp encoded by pCP20 resulting in replacement of fljBA with an ~80-bp scar sequence. The deletion was verified by amplification using primers fljBAF3 (SEQ ID NO:27) and fljBAR2 (SEQ ID NO:28) that are outside the deleted region and the PCR product from CVD 1925 was sequenced (SEQ ID NO:39).

Figure 5:
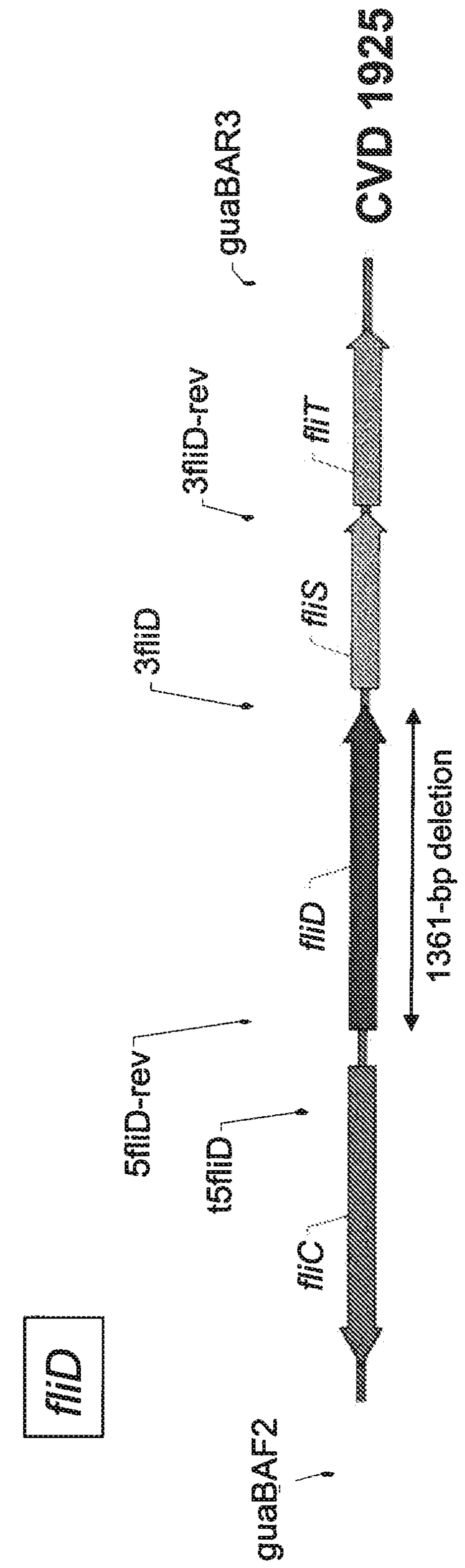
FIG. 5. Deletion of chromosomal fliD from attenuated *Salmonella enterica* serovar *Typhimurium* vaccine strain CVD 1925 using lambda Red-mediated mutagenesis.

For deletion of fliD a slightly different approach was taken. DNA upstream of fliD was amplified using primers t5fliD (SEQ ID NO:29) and t5fliD-rev (SEQ ID NO:30) and DNA downstream of fliD was amplified using primers 3fliD (SEQ ID NO:33) and 3fliD-rev (SEQ ID NO:34) (FIG. 5). The kanamycin resistance cassette from pKD13 was amplified using primers 5FRT-aph (SEQ ID NO:31) and 3FRT-aph (SEQ ID NO:32), and the complete ΔfliD-aph cassette was assembled using unique restriction enzyme sites engineered within the individual cassettes. As with the previous mutations of CVD 1925, this ΔfliD-aph $Km^R$ cassette was integrated into the genome by homologous recombination using lambda Red recombinase and then removed using Flp encoded by pCP20 resulting in replacement of fliD with an ~80-bp scar sequence. The deletion was verified by amplification using primers outside the deleted region using primers g1020 (SEQ ID NO:35) and g1028 (SEQ ID NO:36) and the PCR product from CVD 1925 was sequenced (SEQ ID NO:40).

Figure 6:
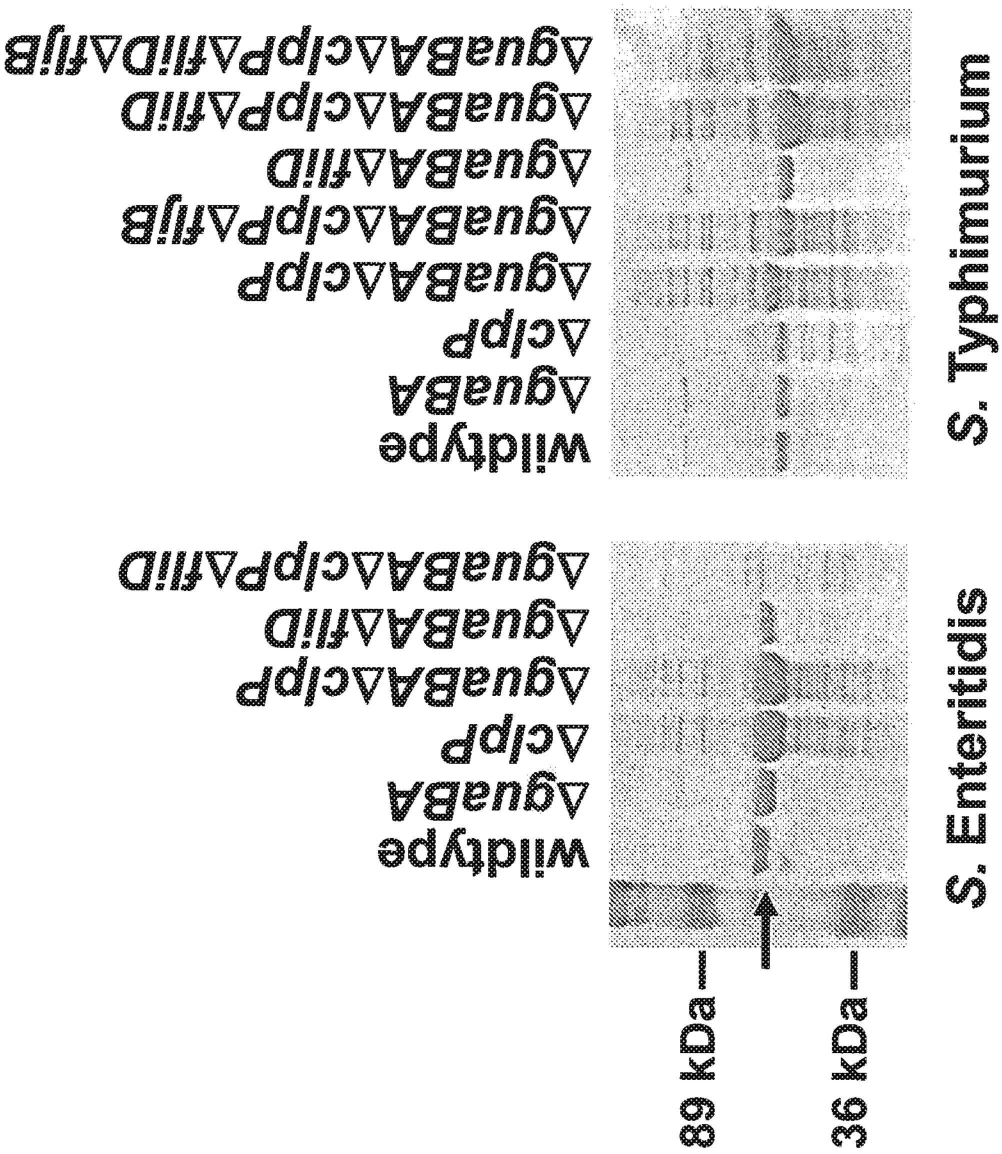
FIG. 6. Expression of flagella in the supernatants of attenuated NTS strains derived from *Salmonella enterica* serovar *Typhimurium* 177 and *Salmonella enterica* serovar *Enteritidis* R11.

To ascertain which of these strains might be most useful for purification of FliC, we examined production of flagellin in supernatants using SDS-PAGE gels stained with Coomassie brilliant blue. As shown in FIG. 6, introduction of ΔclpP significantly improved production of flagella (red arrow; 51.6 kDa) in both *S. Enteritidis* and *S. Typhimurium*. However, further introduction of ΔfliD into *S. Enteritidis* ΔguaBAΔclpP strains seemed to reduce FliC production. The highest levels of FliC production in attenuated strains of *S. Typhimurium* strains were observed in ΔguaBAΔclpPΔfliDΔfljBA strain CVD 1925. As expected, when examined for motility, ΔguaBAΔclpP strains appeared to be hyper-motile and ΔguaBAΔclpPΔfliD strains hyper-expressing FliC monomers were non-motile. For our first attempt at synthesis of an OPS-FliC conjugate vaccine, we chose to focus on the attenuated *S. Enteritidis* candidate vaccine strain CVD 1941 (ΔguaBAΔclpP).

Example 2

Synthesis of an OPS-FliC Conjugate Vaccine Against *S. Enteritidis*

Purification of Flagella from CVD 1941.

Figure 7:
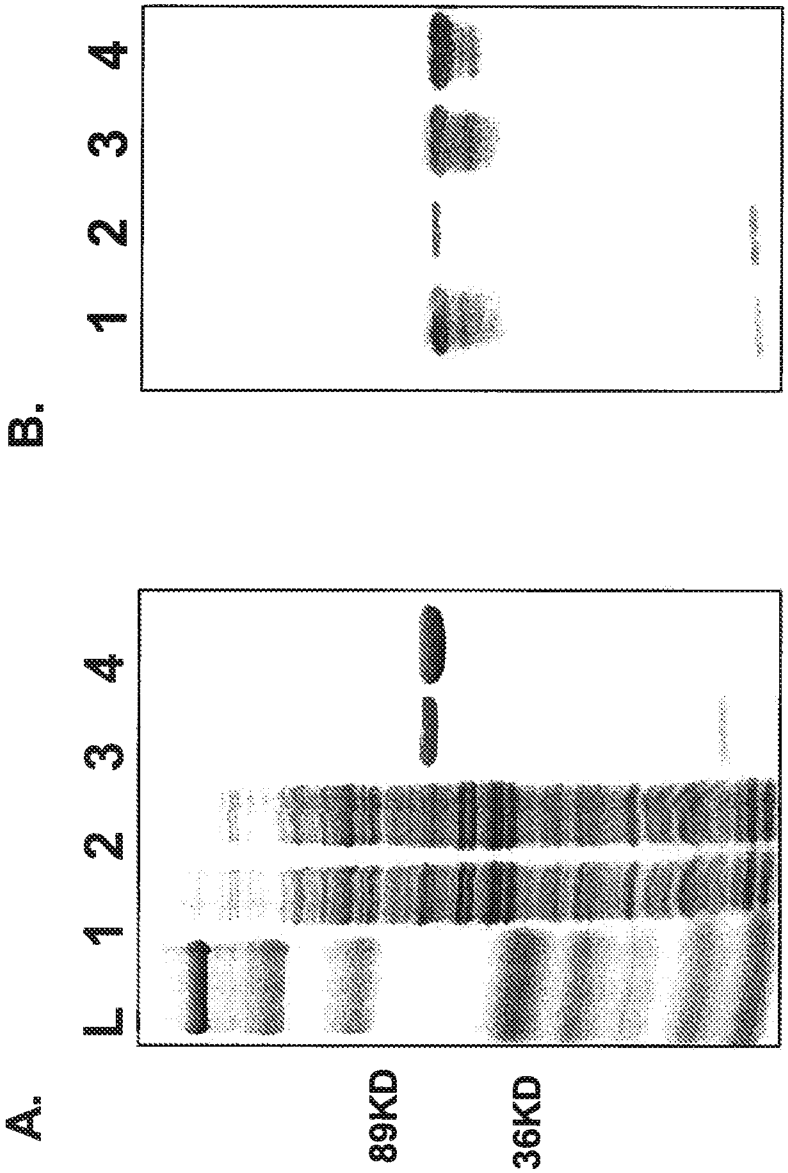
FIG. 7. Purification of *Salmonella Enteritidis* Flagella. *Salmonella* Flagella were isolated as described utilizing mechanical shearing followed by differential centrifugation. Protein samples were analyzed by SDS-PAGE followed by staining with Coomasie dye (A), or by transfer to a PVDF membrane followed by western blot analysis with a monoclonal antibody specific for bacterial flagellin (B). Lane 1: *Salmonella* cells; lane 2: 10KxG centrifugation resuspended *Salmonella* cell pellet following mechanical shearing; lane 3: 10KxG centrifugation sheared cell supernatant; lane 4: 100, 000KxG precipitated flagella material.

Several methods were tested for flagellin purification including: 1] an acidic pH2 method used to disaggregate flagella from intact cells at low pH, 2] a mechanical shearing method used to remove whole flagella from intact cells, 3] a heating method used to disaggregate flagella from intact cells, and 4] purification of passively shed flagella from bacterial supernatant. Each method was assessed for purity of the final flagellin prep, yield of protein, and ease of use. Of these, utilization of the commonly used shear method for flagellin production was found to provide the highest yield and purity with the greatest ease of use. Briefly the shear method utilizes a mechanical disruption of flagella on the surface of cells through processing in a Waring blender. Sheared flagella are then separated from large cellular debris particles through centrifugation at 10,000×g that will separate debris from intact flagella filaments. The 10,000×g supernatant is then subjected to 100,000×g centrifugation to pellet high molecular weight large flagella structures, leaving free low-molecular weight proteins and complexes in the supernatant. The whole flagella obtained from the 100,000×g centrifugation are further depleted of contaminating LPS by heating to disaggregate the flagellar filaments into individual proteins, followed by filtration through a 100 kDa molecular weight cut-off (MWCO) Amicon ultrafiltration device. Protein purity and integrity were assessed using SDS-PAGE gels stained with Coomassie brilliant blue. LPS contamination was assessed by the *Limulus Amebocyte* Lysate Assay with chromogenic endpoint analysis. As shown in FIG. 7, the resulting preparation was highly enriched for flagellin protein (lane 4). The enriched flagellin polymer preparation was disaggregated into monomers by heat dispersion at 70 degrees C. for 15 minutes and passed through a 100 KD Molecular Weight Cutoff Amicon Ultrafiltration unit. The resulting flagellin monomer sample (FIG. 7A, lane 3) contained very low levels of LPS, and was judged suitable for conjugation to polysaccharide.

Purification of LPS, and Generation of OPS from CVD 1941.

For purification of LPS, a method was developed in which a suspension of *Salmonella* was lysed in the presence of nuclease (to degrade bacterial DNA and RNA) by mechanical pressure using a French Press. Lysed cells were further treated with protease to degrade bacterial proteins. LPS was then separated from degraded cellular debris by ethanol precipitation in the presence of excess magnesium. Preparations were further purified from contaminating protein by phenol extraction. The resulting LPS was analyzed on SDS-PAGE gels and visualized by silver stain analysis. As shown in FIG. 8A, LPS preparations were determined to be of high purity. Final preparation of core-OPS polysaccharide for use in conjugation reactions involved removal of Lipid A by mild acid treatment at 100° C. for 1.5 hours in the presence of 1% acetic acid. Free Lipid A was removed by centrifugation at 100,000×g for 5 hours to pellet insoluble Lipid A complexes. The supernatant from the 100,000×g centrifugation was assessed by *Limulus Amebocyte* Lysate assay to be depleted of Lipid A. High molecular weight OPS suitable for conjugation was obtained by size exclusion chromatography (FIG. 8B). Polysaccharide concentration in elution fractions was monitored by assay with resorcinol with LPS as a standard. High molecular weight fractions were selected for use in conjugation.

Synthesis of an *S. Enteritidis* OPS-FliC Conjugate Vaccine.

Isolated monomeric flagellin was concentrated using a 10 kDa MWCO Amicon Ultrafiltration device, and then directly conjugated in approximately equivalent amounts (gram:gram) with core-OPS polysaccharide that had been derivatized and activated beforehand with CDAP chemistry. 3 mg of High Molecular weight OPS (HMW-OPS) in 10 mM Borate buffer and 150 mM NaCl at pH8.6 was added to 5 mg of 100 mg/ml CDAP in Acetonitrile. The pH was adjusted to 9.9 with TEA. At 2.5 minutes, 3 mg of flagellin monomer protein was added. The reaction was incubated at 25 degrees C. for 1.5 hours, 18 hours at 4 degrees C., and then −20 degrees C. for 4 days. The reaction was then quenched with 2M glycine. Initial assessment of conjugation was accomplished by analytical SEC-HPLC and monitoring for protein elution by UV spectroscopy absorbance at 280 nm. Evidence of conjugation was seen by broadening and flattening of the defined peaks in the elution profile, with broad peaks between 6 and 9 minutes which were not observed in the retention peaks from the unconjugated material (data not shown). The resulting conjugate was also analyzed by SDS-PAGE gels stained with Coomassie brilliant blue for protein (FIG. 9A), Emerald Green staining for polysaccharide (FIG. 9B), as well as transferred to PVDF membranes and analyzed by Western blot with a monoclonal antibody (15D8, Bioveris) for flagellin (FIG. 9C). As shown in FIGS. 9A and B, lane 4, evidence of conjugation between OPS and FliC is clearly seen in the high molecular weight species observed above the protein band corresponding to unreacted FliC, that double stains positive for both protein and polysaccharide; further evidence of successful conjugation is indicated by the fact that these higher molecular weight species are recognized by an antibody specific for flagellin, FIG. 9C, lane 2. As controls, purified LPS samples separated in FIG. 9A, lane 1 did not stain with the Coomassie protein stain, and strongly stained for polysaccharide by Emerald Green stain (FIG. 9B, lane 1) with the expected banding pattern characteristic of LPS. Purified flagellin samples separated in FIG. 9A, lane 3 strongly stained with Coomasie dye, but not with Emerald Green. The flagellin protein was also strongly recognized by anti-flagellin antibody (FIG. 9C, lane 1). Flagellin-High Molecular Weight OPS conjugates were purified from un-reacted Flagellin and OPS components by size fractionation with the use of size exclusion chromatography (FIG. 10A). High molecular weight fractions that eluted prior to unreacted flagellin (FIG. 10A, lanes 8-11) were pooled and deemed suitable for use in vaccination against the homologous NTS strains that they were derived from.

Example 3

Purification of FliC Monomers from *Salmonella* Mutants Lacking fliD

Initial purification efforts focused on the removal of contaminating LPS from flagellin preparations recovered from the bacterial supernatants, utilizing sequential ion-exchange column chromatography steps. For the ion exchange purifications, the sample was held at a pH below the isoelectric point of flagellin, but above that of LPS, thus causing the two molecules to have overall net opposite charges since flagellin will have converted to a net positive charge under these conditions, while LPS will maintain a net negative charge. Endotoxin content of the purified material was assayed using a *Limulus Amebocyte* lysate (LAL) assay. SDS-PAGE analysis indicated that the supernatant was effectively concentrated, and flagellin was bound/eluted as expected through the ion-exchange material. Using this method, endotoxin contamination was reduced by ~90%.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

What is claimed is:

1. A method of inducing an immune response, comprising administering to a subject in need thereof an immunologically-effective amount of a *Salmonella enterica* serovar conjugate, wherein the conjugate consists essentially of an O polysaccharide (OPS) covalently linked to a flagellin protein, wherein the serovar is selected from the group consisting of *S. Typhimurium* and *S. Enteritidis*.

2. The method of claim 1, wherein the flagellin protein is a Phase 1 flagella protein.

3. The method of claim 1, wherein the conjugate is made from a serovar that has at least one attenuating mutation selected from group consisting of an attenuating mutation in the guaBA locus and the clpPX locus.

4. The method of claim 1, wherein the conjugate is administered parenterally.

5. The method of claim 4, wherein prior to administering the conjugate, the subject is administered an attenuated strain of the serovar.

6. The method of claim 5, wherein said strain is orally administered to the subject.

7. The method of claim 6, wherein said attenuated strain of the serovar has at least one attenuating mutation selected from group consisting of an attenuating mutation in the guaBA locus and the clpPX locus.

8. The method of claim 7, wherein said subject is a human.

9. The method of claim 2, wherein said effective amount is between about 0.01 μg and 10 μg.

10. The method of claim 9, wherein said Phase 1 flagella protein is covalently linked to said OPS either directly or using a linker.

11. The method of claim 10, wherein said linker is selected from the group consisting of 1-cyano-4-dimethylaminopyridinium tetrafluoroborate, adipic acid dihydrazide, ϵ-aminohexanoic acid, chlorohexanol dimethyl acetal, D-glucuronolactone and p-nitrophenylethyl amine.

12. The method of claim 11, wherein said linker is 1-cyano-4-dimethylaminopyridinium tetrafluoroborate.

13. The method of claim 8, wherein said conjugate is combined with a pharmaceutically acceptable carrier in a pharmaceutical composition.

14. A composition comprising a *Salmonella enterica* serovar conjugate, wherein the conjugate consists essentially of an O polysaccharide (OPS) covalently linked to a flagellin protein, wherein the serovar is selected from the group consisting of *S. Typhimurium* and *S. Enteritidis.*

15. The composition of claim 14, wherein the flagellin protein is a Phase 1 flagella protein.

16. The composition of claim 15, wherein the conjugate is made from a serovar that has at least one attenuating mutation selected from group consisting of an attenuating mutation in the guaBA locus and the clpPX locus.

17. A *Salmonella enterica* serovar strain, wherein said strain has attenuating mutations in the guaBA locus and the clpPX locus and said serovar is selected from the group consisting of *S. Typhimurium* (Group B) and *S. Enteritidis* (Group D).

18. The *Salmonella* serovar strain of claim 17, wherein said serovar is *S. Typhimurium* (Group B).

19. The *Salmonella* serovar strain of claim 17, wherein said serovar is *S. Enteritidis* (Group D).

20. The *Salmonella* serovar strain of claim 17, wherein said attenuating mutation is an attenuating mutation that reduces the level of expression of said loci, or blocks expression of said loci.

* * * * *

SEQUENCE LISTING

<160> NUMBER OF SEQ ID NOS: 40

<210> SEQ ID NO 1
<211> LENGTH: 1578
<212> TYPE: DNA
<213> ORGANISM: Salmonella enterica

<400> SEQUENCE: 1
atgacggaaa acattcataa gcatcgcatc ctcattctgg acttcggttc tcagtacact 60
caactggttg cgcgccgcgt gcgtgagctg ggtgtttact gtgaactgtg ggcgtgggat 120
gtgacagaag cacaaattcg tgacttcaac ccaagcggca ttattctttc cggcggcccg 180
gaaagcacca ccgaagaaaa cagcccgcgc gcgccgcagt atgtctttga agcaggcgtg 240
ccggtatttg gcgtttgcta tggtatgcag accatggcga tgcagcttgg cggtcatgta 300
gaaggttcta atgagcgtga atttggttat gcgcaggtcg aagtgttgac cgacagcgcg 360
ctggttcgcg gtattgaaga ttccctgacc gcagacggca aaccgctgct ggacgtgtgg 420
atgagccacg gcgataaagt gacggcgatt ccgtccgact tcgtgaccgt cgccagcacc 480
gagagctgcc cgttcgccat tatggccaac gaagaaaaac gcttctacgg cgtacagttc 540
cacccggaag tgactcacac ccgccagggt atgcgcatgc tggagcgttt tgtacgcgat 600
atctgccagt gtgaagcgtt gtggacgccg gcgaagatca tcgatgacgc cgtggcgcgc 660
attcgcgagc aggtaggcga cgataaagtg atcctcggtc tctccggcgg cgtggattct 720
tccgtcaccg ccatgctgct gcaccgcgcg atcggtaaaa atctgacctg tgttttcgtc 780
gacaacggcc tgttgcgcct gaacgaagcc gagcaggtga tggacatgtt tggcgaccat 840
tttggtctga acattgttca cgtaccggca gaagatcgct tcctgtccgc gctggctggt 900
gagaacgatc cggaagccaa gcgtaagatc atcggccgcg ttttcgttga agtgttcgac 960
gaagaagcgc tgaaactgga agacgtgaaa tggctggcgc agggcaccat ctaccctgac 1020
gttatcgaat ctgcggcgtc tgcaaccggt aaagcgcacg tcatcaaatc tcaccacaat 1080
gtcggcggcc tgccgaaaga gatgaagatg gggctggttg aaccgctgaa agagctgttc 1140
aaagacgaag tgcgtaagat tggtctggag ctgggcctgc cgtacgacat gctgtatcgc 1200
catccgttcc cggggccggg cctcggcgtg cgcgtactgg gcgaagtgaa gaaagagtac 1260
tgcgacctgc tgcgtcgcgc ggacgctatc ttcattgaag agctgcgcaa agcggatctg 1320
tacgacaaag tcagtcaggc gtttaccgtc ttcctgccgg tccgttccgt aggcgtgatg 1380
ggcgatggtc gtaagtacga ttgggttgtc tctctgcgtg ctgtcgaaac catcgacttt 1440
atgaccgcac actgggcaca tctgccgtat gatttcctgg gtcgtgtttc caaccgcatc 1500
atcaatgaag tcaacgggat ttcccgtgtg gtgtatgaca tcagcggtaa accaccagct 1560
accattgagt gggaataa 1578

<210> SEQ ID NO 2
<211> LENGTH: 1578
<212> TYPE: DNA
<213> ORGANISM: Salmonella enterica

<400> SEQUENCE: 2
atgacggaaa acattcataa gcatcgcatc ctcattctgg acttcggttc tcagtacact 60
caactggttg cgcgccgcgt gcgtgagctg ggtgtttact gtgaactgtg ggcgtgggat 120
gtgacagaag cacaaattcg tgacttcaac ccaagcggca ttattctttc cggcggcccg 180
gaaagcacca ccgaagaaaa cagcccgcgc gcgctgcagt atgtctttga agcaggcgtg 240

-continued

```
ccggtatttg gcgtttgcta tggtatgcag accatggcga tgcagcttgg cggtcatgta    300

gaaggttcta atgagcgtga atttggttat gcgcaggtcg aagtgttgac cgacagcgcg    360

ctggttcgcg gtattgaaga ttccctgacc gcagacggca aaccgctgct ggacgtgtgg    420

atgagccacg gcgataaagt gacggcgatt ccgtccgact tcgtgaccgt cgccagcacc    480

gagagctgcc cgttcgccat tatggccaac gaagaaaaac gcttctacgg tgtacagttc    540

cacccggaag tgactcacac ccgccagggt atgcgcatgc tggagcgttt tgtacgcgat    600

atctgccagt gtgaagcgtt gtggacgccg gcgaagatca tcgacgacgc cgtggcgcgc    660

attcgcgagc aggtgggcga cgacaaagtg atcctcggcc tctctggtgg cgtggattct    720

tccgtcaccg caatgctgct gcaccgcgcg atcggtaaaa atctgacctg tgtattcgtc    780

gacaacggcc tgctgcgtct caacgaagcc gagcaggtga tggacatgtt tggcgaccat    840

tttggcctga atatcgttca cgtaccggca gaagagcgct tcctgtccgc gctggctggc    900

gagaacgatc cggaagccaa gcgtaagatc atcggtcgtg tttttgtaga agtgttcgac    960

gaagaagcgc tcaaactgga agacgtgaag tggctggcgc aaggcaccat ttaccctgac   1020

gttatcgaat ctgcggcgtc tgcaaccggt aaagcgcacg tcatcaaatc tcaccacaat   1080

gtcggcggct tgccgaaaga gatgaagatg gggctggttg aaccgctgaa agagctgttc   1140

aaagacgaag tgcgtaagat tggtctggag ctgggcctgc cgtatgacat gctgtatcgc   1200

catccgttcc cggggccggg cctcggcgtt cgtgttctgg gtgaagtgaa gaaagagtac   1260

tgcgacctgc tgcgccgtgc tgacgctatc ttcattgaag agctgcgcaa agcggatctg   1320

tacgacaaag tcagtcaggc gtttaccgtc ttcctgccgg ttcgttccgt tggcgttatg   1380

ggcgatggtc gtaagtatga ctgggttgtc tctctgcgtg ccgtcgaaac catcgacttt   1440

atgaccgcac actgggcgca cctgccgtat gacttcctcg gtcgcgtttc caaccgcatc   1500

atcaatgaag tcaacgggat ttcccgtgtg gtgtatgaca tcagcggtaa accgccggct   1560

accattgagt gggaataa                                                1578
```

```
<210> SEQ ID NO 3
<211> LENGTH: 1467
<212> TYPE: DNA
<213> ORGANISM: Salmonella enterica

<400> SEQUENCE: 3
```

```
atgctacgta tcgctaaaga agctctgacg tttgacgacg tcctccttgt tcccgctcac     60

tccaccgttt tgccgaatac tgccgatctc agcacgcagt tgacgaaaac tattcgtctg    120

aatattccta tgctttctgc ggcgatggac accgtgacgg aagcgcgcct ggcaattgcc    180

ctggcccagg aaggcggcat tggttttatc cacaaaaaca tgtctattga gcgccaggcg    240

gaagaagttc gccgcgtgaa gaaacacgag tccggcgtag tgaccgaccc gcagaccgtc    300

ctgccaacca ccacgttgca tgaagtgaaa gccctgaccg agcgtaacgg ttttgcgggc    360

tatccggtgg tgactgaaga taacgagctg gtgggtatca tcaccggtcg tgacgtgcgt    420

tttgtgactg acctgaacca gccggtgagt gtctacatga caccgaaaga gcgtctggtg    480

accgttcgtg aaggcgaagc ccgtgaagtc gtgctggcaa aaatgcacga aaaacgcgta    540

gaaaaagcgc tggtcgttga tgataacttc catctgcttg gcatgattac cgtaaaagat    600

ttccagaaag cggaacgtaa accaaactcc tgtaaagatg agcagggccg tttacgtgtc    660

ggcgcggcgg tcggcgcagg cgcgggcaac gaagagcgcg ttgacgcgct ggtggcggca    720
```

-continued

```
ggcgttgacg tactgctgat cgactcctct cacggtcact ctgaaggcgt gttgcaacgt    780

atccgtgaga cgcgtgctaa atatcctgac ctgcaaatca tcggcggcaa cgttgcgacg    840

ggcgcaggcg ctcgcgcact ggcggaagcc ggttgcagcg cggtgaaagt gggtatcggc    900

ccgggttcca tctgtacgac tcgtatcgtg actggtgtgg gcgttccgca gatcaccgct    960

gtttctgacg cggtggaagc gctggaaggc accgggattc cggttatcgc tgacggcggt   1020

atccgtttct ccggcgacat cgccaaagcc atcgccgcag gcgcgagcgc ggtaatggtg   1080

ggttctatgc tggccggtac cgaagaatcc ccgggcgaaa tcgaactcta ccagggccgt   1140

tcttacaaat cttatcgcgg tatgggttct ctgggcgcga tgtccaaagg ttcctccgac   1200

cgttacttcc agagcgacaa cgccgccgac aaactggtgc cggaaggtat cgaaggccgc   1260

gtagcctata aaggtcgcct gaaagagatc attcaccagc agatgggcgg cctgcgctcc   1320

tgtatggggc tgaccggttg tgctaccatc gacgaactgc gtactaaagc ggagtttgtg   1380

cgtatcagcg gtgcgggtat ccaggaaagc cacgttcacg acgtgaccat caccaaagag   1440

tccccgaact accgtctggg ctcctga                                       1467


<210> SEQ ID NO 4
<211> LENGTH: 1467
<212> TYPE: DNA
<213> ORGANISM: Salmonella enterica

<400> SEQUENCE: 4

atgctacgta tcgctaaaga agccctgacg tttgacgacg tcctccttgt tcccgctcac     60

tccaccgttt tgccgaatac tgccgatctc agcacgcagt tgacgaaaac tattcgtctg    120

aatattccta tgctttctgc ggcgatggac accgtgacgg aagcgcgcct ggcaattgcc    180

ctggcccagg aaggcggcat tggttttatc cacaaaaaca tgtccattga gcgccaggcg    240

gaagaagttc gccgcgtgaa gaaacacgag tccggcgtag tgaccgaccc gcagaccgtc    300

ctgccaacca ccacgttgca tgaagtgaaa gccctgaccg agcgtaacgg ttttgcgggc    360

tatccggtgg tgactgaaga taacgagctg gtgggtatca tcaccggtcg tgacgtgcgt    420

tttgtgactg acctgaacca gccggttagc gtttacatga cgccgaaaga gcgtctggtg    480

accgttcgtg aaggcgaagc ccgtgaagtc gtgctggcaa aaatgcacga aaaacgcgta    540

gaaaaagcgc tggtcgttga tgataacttc catctgcttg gcatgattac cgtaaaagat    600

ttccagaaag cggaacgtaa accaaactcc tgcaaagatg agcagggccg tttacgtgtc    660

ggcgcggcgg tcggcgcagg cgcgggcaac gaagagcgcg ttgacgcgct ggtggcggca    720

ggcgttgacg tactgctgat cgactcctct cacggtcatt cagaaggcgt gttgcaacgt    780

atccgtgaaa cccgtgctaa atatcctgac ctgcaaatca tcggcggcaa cgtcgcgaca    840

ggcgcaggcg ctcgcgcact ggcggaagcc ggttgcagcg cggtgaaagt cggtattggc    900

ccgggttcca tctgtaccac tcgtatcgtg actggcgtgg gcgttccgca gatcaccgct    960

gtttctgacg cagttgaagc gctggaaggt accggtattc cggttatcgc tgacggcggt   1020

atccgtttct ccggcgacat agccaaagcg attgccgcag gtgcaagcgc ggtaatggtg   1080

ggttccatgc tggcgggtac ggaagaatcc ccgggcgaaa tcgaactcta ccagggccgt   1140

tcttacaaat cttaccgcgg catgggctcg ctgggtgcga tgtccaaagg ttcctccgac   1200

cgttacttcc agagcgacaa cgccgctgac aaactggtgc cggaaggtat cgaaggtcgc   1260

gtagcctata aaggtcgcct gaaagagatc attcaccagc agatgggcgg cctgcgctcc   1320

tgtatggggc tgaccggttg tgctaccatc gacgaactgc gtactaaagc ggagtttgtg   1380
```

cgtatcagcg gtgcgggcat tcaggaaagc cacgttcacg acgtgaccat caccaaagag 1440
tccccgaact accgtctggg ctcctga 1467

<210> SEQ ID NO 5
<211> LENGTH: 624
<212> TYPE: DNA
<213> ORGANISM: Salmonella enterica

<400> SEQUENCE: 5
atgtcataca gcggagaacg agataatttg gcccctcata tggcgctggt gccgatggtc 60
attgaacaga cctcacgcgg tgagcgctct tttgatatct attctcgtct acttaaggaa 120
cgcgtcatat ttctgaccgg ccaggtcgaa gaccatatgg ctaacctgat cgtggcgcag 180
atgctgttcc tggaagcgga aaacccggaa aaagatatct atctgtacat taattctcct 240
ggcggcgtaa ttactgcggg gatgtccatc tatgacacca tgcagtttat taagccagac 300
gtcagcacca tttgtatggg acaggcggcc tctatggggg cgtttctgct gactgccggg 360
gcgaaaggca aacgtttctg cttgccgaac tctcgcgtca tgatccacca gccgctgggc 420
ggctaccagg gccaggcgac ggatattgaa attcacgccc gcgaaatttt gaaagtaaaa 480
gggcgcatga atgaacttat ggcgcatcat acgggtcaat ctcttgagca gattgaacgt 540
gatactgagc gcgatcgctt cctctccgcg cctgaagcgg tagagtacgg tttggttgac 600
tcaattttga cccatcgtaa ttga 624

<210> SEQ ID NO 6
<211> LENGTH: 624
<212> TYPE: DNA
<213> ORGANISM: Salmonella enterica

<400> SEQUENCE: 6
atgtcataca gcggagaacg agataatttg gcccctcata tggcgctggt gccgatggtc 60
attgaacaga cctcacgcgg tgagcgctct tttgatatct attctcgtct acttaaggaa 120
cgcgtcatat ttctgaccgg ccaggtcgaa gaccatatgg ctaacctgat cgtggcgcag 180
atgctgttcc tggaagcgga aaacccggaa aaagatatct atctgtacat taattctcct 240
ggcggcgtaa ttactgcggg gatgtccatc tatgacacca tgcagtttat taagccagac 300
gtcagcacca tttgtatggg acaggcggcc tctatggggg cgtttctgct gactgccggg 360
gcgaaaggca aacgtttctg cttgccgaac tctcgcgtca tgatccacca gccgctgggc 420
ggctaccagg gccaggcgac ggatattgaa attcacgccc gcgaaatttt gaaagtaaaa 480
gggcgcatga atgaacttat ggcgcatcat acgggtcaat ctcttgagca gattgaacgt 540
gatactgagc gcgatcgctt cctctccgcg cctgaagcgg tagagtacgg tttggttgac 600
tcaattttga cccatcgtaa ttga 624

<210> SEQ ID NO 7
<211> LENGTH: 1272
<212> TYPE: DNA
<213> ORGANISM: Salmonella enterica

<400> SEQUENCE: 7
atgacagata aacgcaaaga tggctcgggc aaattgttgt actgctcttt ttgcggcaaa 60
agccagcatg aagtgcgcaa gctgattgcc ggtccatccg tgtatatctg cgacgaatgc 120
gtcgatttat gtaacgacat tattcgcgaa gaaattaaag aagttgctcc gcaccgtgaa 180

-continued

```
cgtagtgcgc tgccgacgcc gcatgaaatt cgtacccacc tggacgatta cgttatcggc    240

caggagcagg cgaaaaaagt gctggcgctg gcggtctata accactacaa gcgtctgcgt    300

aacggcgata ccagcaatgg cgtcgagtta ggtaaaagca acattctgct gattggaccg    360

accggttccg gtaaaacgct gctggcggaa acgctggcgc gcttgctgga tgtgccgttc    420

actatggcgg atgcgaccac gctaaccgaa gcgggttacg ttggtgaaga cgtcgagaat    480

atcattcaga aactgttgca gaaatgcgac tacgacgtgc aaaaagcgca gcgtgggatt    540

gtctacattg atgaaatcga taagatttcg cgtaaatcag acaatccgtc cattacccgc    600

gatgtttccg gcgaaggcgt acagcaggcg ttgctgaaac tgatcgaagg caccgtcgcc    660

gcggttccac cgcagggcgg tcgcaaacat ccgcagcagg agttcttaca ggtagatacc    720

tctaagattc tgtttatctg cggcggcgcg tttgccggtc tggataaagt gatcgctaac    780

cgtgttgaaa ccggctccgg cattggtttt ggcgcgacgg tgaaagcgaa gtccgacaaa    840

gccagcgaag gcgagctgtt gtcgcaggtt gaaccggaag atttgatcaa atttggtctg    900

attcctgagt ttatcggtcg tctgccagtg gtagcgacgc tgaatgaact cagcgaagaa    960

gcgctgattc aaatcctgaa agagccgaaa aatgcgctga ccaagcagta tcaggcgctg   1020

tttaacctgg aaggcgtcga tctggaattc cgtgacgaag cgctggacgc tatcgccagg   1080

aaagcaatgg cgcgtaaaac cggcgcccgt ggcctgcgtt ctatcgtcga agcggcgctg   1140

ctggatacca tgtacgattt gccatctatg gaagacgtcg aaaaagtggt gatcgacgag   1200

tccgttattg ccggtcagag taagccgttg ctgatttacg gcaaaccgga agcgcaggct   1260

tctggcgaat aa                                                        1272
```

<210> SEQ ID NO 8
<211> LENGTH: 1272
<212> TYPE: DNA
<213> ORGANISM: Salmonella enterica

<400> SEQUENCE: 8

```
atgacagata aacgcaaaga tggctcgggc aaattgttgt actgctcttt ttgcggcaaa     60

agccagcatg aagtgcgcaa gctgattgcc ggtccatccg tgtatatctg cgacgaatgc    120

gtcgatttat gtaacgacat tattcgcgaa gaaattaaag aagttgctcc gcaccgtgaa    180

cgtagtgcgc tgccgacgcc gcatgaaatt cgtacccacc tggacgatta cgttatcggc    240

caggagcagg cgaaaaaagt gctggcggtg gcggtctata accactacaa gcgtctgcgt    300

aacggcgata ccagcaatgg cgtcgagtta ggtaaaagca acattctgct gattggaccg    360

accggttccg gtaaaacgct gctggcggaa acgctggcgc gcttgctgga tgtgccgttc    420

actatggcgg atgcgaccac gctaaccgaa gcgggttacg ttggtgaaga cgtcgagaat    480

atcattcaga aactgttgca gaaatgcgac tacgacgtgc aaaaagcgca gcgtgggatt    540

gtctacattg atgaaatcga taagatttcg cgtaaatcag acaatccgtc cattacccgc    600

gatgtttccg gcgaaggcgt acagcaggcg ttgctgaaac tgatcgaagg caccgtcgcc    660

gcggttccac cgcagggcgg tcgcaaacat ccgcagcagg agttcttaca ggtagatacc    720

tctaagattc tgtttatctg cggcggcgcg tttgccggtc tggataaagt gatcgctaac    780

cgtgttgaaa ccggctccgg cattggtttt ggcgcgacgg tgaaagcgaa gtccgacaaa    840

gccagcgaag gcgagctgtt gtcgcaggtt gaaccggaag atttgatcaa atttggtctg    900

attcctgagt ttatcggtcg tctgccagtg gtagcgacgc tgaatgaact cagcgaagaa    960

gcgctgattc aaatcctgaa agagccgaaa aatgcgctga ccaagcagta tcaggcgctg   1020
```

tttaacctgg aaggcgtcga tctggaattc cgtgacgaag cgctggacgc tatcgccagg 1080
aaagcaatgg cgcgtaaaac cggcgcccgt ggcctgcgtt ctatcgtcga agcggcgctg 1140
ctggatacca tgtacgattt gccatctatg gaagacgtcg aaaaagtggt gatcgacgag 1200
tccgttattg ccggtcagag taagccgttg ctgatttacg gcaaaccgga agcgcaggct 1260
tctggcgaat aa 1272

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
gtgtaggctg gagctgcttc 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
attccgggga tccgtcgacc 20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
tgtttatgct gctgatcgaa c 21

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gaagcagctc cagcctacac gggcaatatc tcacctgg 38

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ggtcgacgga tccccggatg ccgataatcc ttcctgtg 38

<210> SEQ ID NO 14
<211> LENGTH: 20

<212> TYPE: DNA
<213> ORGANISM: Artificial Sequence
<220> FEATURE:
<223> OTHER INFORMATION: Description of Artificial Sequence: Synthetic
primer

<400> SEQUENCE: 14
ataacctgga cacttctgag 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 15
ttcgaagtga tcaccccaac 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 16
tatttgggct gaatcgccac 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 17
taagcgtcgt gtagttgtcg 20

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 18
gaagcagctc cagcctacac attacatttc cgtctcctgg 40

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 19
ggtcgacgga tccccggaat tgatgccctg gacgcaagtg 40

<210> SEQ ID NO 20
<211> LENGTH: 20
<212> TYPE: DNA

<213> ORGANISM: Artificial Sequence
<220> FEATURE:
<223> OTHER INFORMATION: Description of Artificial Sequence: Synthetic
primer

<400> SEQUENCE: 20
taacgtaatc gtccaggtgg 20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21
agaaacaggc tctggagctg 20

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 22
acggcgtgtt tacaggaaaa acgaaagggg 30

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 23
tatgacactt gatcatgtga tg 22

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 24
gaagcagctc cagcctacac ccaataaatc gtgtggctg 39

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: Synthetic
primer

<400> SEQUENCE: 25
ggtcgacgga tccccggaat cgcctacggt aataaaaaat tc 42

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
tgagaacttc agcaaatcga c 21

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
acgtcataaa tcgaacaagt cg 22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
agcttcagca ttgcatcagc 20

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
gaattctcac gcacacgctg cagg 24

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gctagcacct aatgatgaaa ttgaagccat gc 32

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
gaattcgcta gcgctggagc tgcttcgaag ttc 33

<210> SEQ ID NO 32
<211> LENGTH: 33
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 32
ctcgagttcc ggggatccgt cgacctgcag ttc 33

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggatccgcta tgaacaagtc ctgataacag aggt 34

<210> SEQ ID NO 34
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctcgagttaa cgagactcct ggaaagatgc tttcggtgaa atctgc 46

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gattgactga gcagcgcaat acgctg 26

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggtgatttca gcctggatgg agtcga 26

<210> SEQ ID NO 37
<211> LENGTH: 2109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
ctcctgctgg ttacggctga caatttctgc cgctgctgat ggcgtaggcg cgcgcaggtc 60
ggcgacaaaa tcagctatcg tgacgtccgt ttcgtgaccg acggcgctga ccaccggaat 120
gcggctggca aaaatcgccc gcgccacgcg ttcgtcgtta aaactccaca aatcttccag 180
cgaaccgccg ccgcgcccga cgatcagtac atcacattcg ccgcgcgcgt tcgccagttc 240
gatagcacga acgatctgcc ccggcgcgtc gtcgccctgg actgcggttg gatagataat 300
aacgggcagg gatgggtcac gacgctttag cacgtggaga atatcgtgca gcgccgcgcc 360
ggttttcgaa gtgatcaccc caacgcagtg ggccggggag ggcaacggct gtttatgctg 420
ctgatcgaac aagccttcgg cctgcagttt ggcttttagc tgctcatatt tctgctgcaa 480
caagccttcg cccgcgggct gcatactttc ggcgatgatt tgataatcgc cgcgcggctc 540
gtacagcgta atgttggcgc gtaccagcac ctgctgcccg tgctgcgggc ggaacgtcac 600
ccggcgattg ctgttacgga acatcgcaca gcgcacctga gcggtatcgt ctttgagcgt 660
aaagtaccag tggcccgacg caggctgcgt gaaattagaa atctcgccgc tgatccatac 720
ctgtcccatc tcctgttcta acagcagacg aaccgtctgg ttaaggcggc ttacggtaaa 780
aattgaggaa gtttgagagg ataacatgtg agcgggatca aattctaaat cagcaggtta 840
ttcaatcgat agtaacctgc tcacggggga tcgcaagcac tatttgcaaa aaaatgtaga 900
tgcaaccgat tacgttctgt ataatgccgc ggcaatattt attaacctcc caggtgagat 960
attgcccgtg taggctggag ctgcttcgaa gttcctatac tttctagaga ataggaactt 1020
cgaactgcag gtcgacggat ccccggaatg ccgataatcc ttcctgtgtt ttcatgaaca 1080
ggtaaaggtg aatttaaccc tctgttttta cagagggttt ttatttatgt gcattcatga 1140
attttctatg tggcgcacag ttcctgacgg caaatttgac gtaattacga acccacgaag 1200
gttggttgta tcttgccgtg gtcgttgatt tgttctcgtg caaagttatc ggttggtcaa 1260
tgcaaccacg aatgacaaaa gatattgttc tgaatgcgct tctgatggcc gtgtggcgac 1320
gtcatcccca aaaacaggtg ctggttcagt ctgatcaggg tagtcagtac acccgctatg 1380
aatggctgaa attgcacgga ctggagggca gtatgagccg ttgtggcaac tgtcatgaca 1440
atgcggttgc agaaagcttt ttccagctac tgaagcgtga acggataaag aaaaagatct 1500
accaacgact cagaagtgtc caggttatcc gtggcgattc agcccaaata aggggtattt 1560
aaaatatagt aactttattc ttcaactata taaccaacgc ccagctttag cactttcaac 1620
gagcatacca accgttagtg gcttacgcgg atcaggctct ttacttccaa agtactctgg 1680
attcagatag ttgagtatgt caaatccttc tgaatctaca ttccaacgct tgaagtactt 1740
ttgtagaagt tcttcactat cttcaaaaac gagtttaaga tcatccctaa tactggtatc 1800
aagcgtgatg attcgctttg gcccacagag aaagtacttt ttagtgttat attcctgatc 1860
gataaaatcg ataatttctt tctcaatatc tctcattaga agtacgtcca cttaatgcga 1920
tctttaggaa ccgccacacg attaaatgta tctttaatat tacgctggat atcataaatc 1980
gtagtgaatg tcataaccca accgagccag ggtacattac gaccaacgaa acgacctaaa 2040
ttattcgttg agcttagctg taatgagttg atagttttgc ctgtcaacgt tggtaatctg 2100
atcccaggt 2109

<210> SEQ ID NO 38
<211> LENGTH: 1094
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 38
agcgtcgtgt agttgtcggt ctgctgctcg gcgaagtcat tcgtaccaac gagctgaaag 60
cggacgaaga acgcgttaaa ggcctgatcg aagagatggc gtctgcttac gaagatccga 120
aagaagtgat tgagttctac agcaaaaata aagagctgat ggacaatatg cgtaacgtcg 180

```
ctctggaaga acaggctgtt gaagcggttc tggcaaaagc gaaagtgtct gaaaaagcca    240
cttccttcaa tgagctgatg aaccagcagg cgtaattttt cgcgttaaaa gcacgaaatt    300
tgcacaaaaa cccgtcacct ttcagtgacg ggtttttttt gtcacgtatt ttgcatggta    360
agggtgcgaa aaccgcgttt cagtgttagc gttagagcaa aagattgtta tgcttgaatt    420
atggcgatgc cgtacccatt acagagggac tggctgataa tccgtccatc aggttacaat    480
cagtacagca gatttttca atttttatcc aggagacgga aatgtaatgt gtaggctgga    540
gctgcttcga agttcctata ctttctagag aataggaact tcgaactgca ggtcgacgga    600
tccccggaat tgatgccctg gacgcaagtg tgccgctata cacttcatcc ttcacgctac    660
ctcggtgttg gctgccagcg cgcctcccag tgacttactt atgtaagcgc ctgcagagtc    720
gacgagttgc cgccttgatg tagctcgaat gattttgtgt atatactaat gaagggcggc    780
acaacgctga ttagcggctt gcgcctgaga atggcatttg cgtcgtcgtg tgcggcacaa    840
agaacaaaga agaggttttg actcatgaca gataaacgca aagatggctc gggcaaattg    900
ttgtactgct ctttttgcgg caaaagccag catgaagtgc gcaagctgat tgccggtcca    960
tccgtgtata tctgcgacga atgcgtcgat ttatgtaacg acattattcg cgaagaaatt   1020
aaagaagttg ctccgcaccg tgaacgtagt gcgctgccga cgccgcatga aattcgtacc   1080
cacctggacg atta                                                    1094
```

<210> SEQ ID NO 39
<211> LENGTH: 1218
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
cgaacaagtc gttaatgaga atgataataa ttaccaatat catttgtaaa atgcaataac     60
taatatgaca cttgatcatg tgatgatttt ttgcgtaaaa atcgggaaag atgagagcgt    120
taagcggtga agtttggttt caggcttatt tacgcgcgta tggtcgcaca ggcaaagcgc    180
caggattggg gaactggatt cgcataccag acgcccgtgg attattaatg ataacttcgc    240
aaataacctt tcagacaatg aggtaaacgt accgacagca aggtaacggg aaacgtaggg    300
agtagtattg ataacacgtt gcggggcaat ttaatggtgt ccggcggcag atcgtgttct    360
gtgcagactt tccggcgtta aatcccgtat cacctgcgag cctggactat ctctgtggta    420
tcaactctgt aggaatttg tccccttcgt cttcattagc caatgaaacc ggctttaacg    480
tcaccgttcg aatgttgcga acgaacagct ccttatgcgg aatatcgtca ccgctctgcg    540
atttttatag cgcatcagcc acacgattta ttgggtgtag gctggagctg cttcgaagtt    600
cctatacttt ctagagaata ggaacttcga actgcaggtc gacggatccc cggaatcgcc    660
tacggtaata aaaaattccg tgagaaaagt aaaacttagg gggctaccgg aggggaccta    720
atgaacggag gtcatggaag gtattcatcg tgccagactc ttgctcttgt cagaagaagg    780
taaaagtagg ttccgcgacg catttgggtt cacgggcatc ataagagaga tgaacactga    840
taaagtactt tctcctggga taccggaaca gtccaggaaa gagggcagtt acactattgt    900
cgtctggtga tgattactct tcattcatgc ttgccgaacg agttgaagcg atgtaagagg    960
ccgtagctat cgatcccaat aatcccaaaa tttaccaggc cttttatgaa ggctcaaatt   1020
tggctcaatg ggtacgccaa cgccttctgt gatactgtag ggttccaag ttttacatag   1080
```

-continued

```
tgtctaattt aatgctattt gtgggttgat aacccaactc acttcgaact ggtttgtcga   1140

tttgctgaag ttctcaattt gcctgaaggt taattctacg cgctggatga cagctttgct   1200

gatgcaatgc tgaagcta                                                 1218


<210> SEQ ID NO 40
<211> LENGTH: 983
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

ggttgttgtt gatttcgttc agcgcgcctt cagtggtctg cgcaatggag ataccgtcgt     60

tagcgttacg ggaagcctga gtcagacctt tgatgttcgc ggtaaaacgg ttagcaatcg    120

cctgacctgc cgcatcgtct ttcgcgctgt tgatacgcag accggaagac agacgctcga    180

tagcggtgcc cagagcggac tgggatttgt tcaggttatt ctgggtcaac agcgacaggc    240

tgtttgtatt aatgacttgt gccatgatct tttccttatc aattacaact tgatgttatt    300

gggctgttgc ccacggtttc tcaccgtaac ccttgtatcg gcacctgaat ttcgaacttt    360

agaaaatttt tcacttcccc cgatcttttt cttaggcggc gaaatagccg ctttatgcat    420

cattattccg cgcattattt ttgcaaaatt atcattaaac tttgcctcca gattgccgat    480

aacgcgctta actactgttt gcaatcaaaa aggaagaagg catggcttca atttcatcat    540

taggtgctag cgctggagct gcttcgaagt tcctatactt tctagagaat aggaacttcg    600

aactgcaggt cgacggatcc gctatgaaca agtcctgata acagaggtca ccatgtacac    660

cgcgagcggt atcaaagctt atgcgcaagt cagcgtggaa agcgccgtga tgagcgccag    720

cccgcatcag ttgattgaaa tgttgtttga tggcgcgaat agcgctctgg tgcgcgctcg    780

cctgttttta gaacaaggcg atgttgtcgc gaaaggtgaa gcgttaagca aagccatcaa    840

tattatcgat aacgggctga aagccggcct cgatcaggaa aaaggcggtg agattgcgac    900

gaatctttcc gagctatacg actatatgat tcgccgttta ctgcaggcta atttgcgtaa    960

cgacgctcag gccatcgaag aag                                            983
```